(12) United States Patent
Fu et al.

(10) Patent No.: US 9,402,926 B2
(45) Date of Patent: *Aug. 2, 2016

(54) FLUORESCENT MAGNETIC NANOPROBES, METHODS OF MAKING, AND METHODS OF USE

(71) Applicant: The Board of Trustees of the Leland Stanford Junior University, Palo Alto, CA (US)

(72) Inventors: Aihua Fu, Mountain View, CA (US); Shan X. Wang, Palo Alto, CA (US); Sanjiv S. Gambhir, Portola Valley, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/255,210

(22) Filed: Apr. 17, 2014

(65) Prior Publication Data
US 2014/0227190 A1 Aug. 14, 2014

Related U.S. Application Data

(63) Continuation of application No. 12/460,007, filed on Jul. 10, 2009, now Pat. No. 8,722,017.

(60) Provisional application No. 61/079,485, filed on Jul. 10, 2008.

(51) Int. Cl.
| | | |
|---|---|---|
| *A61B 5/055* | (2006.01) | |
| *A61K 51/12* | (2006.01) | |
| *A61K 49/00* | (2006.01) | |
| *A61K 49/18* | (2006.01) | |
| *B82Y 5/00* | (2011.01) | |
| *G01N 33/543* | (2006.01) | |
| *G01N 33/58* | (2006.01) | |

(52) U.S. Cl.
CPC ......... *A61K 51/1244* (2013.01); *A61K 49/0002* (2013.01); *A61K 49/0032* (2013.01); *A61K 49/0093* (2013.01); *A61K 49/1833* (2013.01); *A61K 49/1848* (2013.01); *B82Y 5/00* (2013.01); *G01N 33/5434* (2013.01); *G01N 33/582* (2013.01); *G01N 33/587* (2013.01)

(58) Field of Classification Search
CPC ........... A61K 51/1244; A61K 49/0002; A61K 49/0032; A61K 49/0093; A61K 49/1833; A61K 49/1848; B82Y 5/00; G01N 33/5434; G01N 33/582; G01N 33/587
USPC ...................................................... 424/9.32
See application file for complete search history.

(56) References Cited

U.S. PATENT DOCUMENTS

| | | | |
|---|---|---|---|
| 2003/0092029 A1* | 5/2003 | Josephson et al. ................ 435/6 |
| 2004/0208825 A1 | 10/2004 | Carpenter | |
| 2005/0130167 A1 | 6/2005 | Bao | |
| 2005/0265922 A1 | 12/2005 | Nie | |
| 2006/0018835 A1 | 1/2006 | Lucien Malenfant et al. | |
| 2006/0025713 A1 | 2/2006 | Rosengart | |
| 2006/0093555 A1 | 5/2006 | Torres et al. | |
| 2006/0105052 A1 | 5/2006 | Acar et al. | |
| 2006/0263908 A1 | 11/2006 | Hirai | |
| 2006/0292555 A1 | 12/2006 | Xu | |
| 2007/0140974 A1* | 6/2007 | Torres et al. ............... 424/9.323 |
| 2011/0165077 A1 | 7/2011 | Qian et al. | |

FOREIGN PATENT DOCUMENTS

WO 2005062741 A2 7/2005

OTHER PUBLICATIONS

Gerion et al. J Phys Chem B. 2001, 105, 8861-8871.
Lewin, M., Carlesso, N., Tung, C., Tang, X., Cory, D., Scadden, D., Weissleder, R. Tat peptide-derivatized magnetic nanoparticles allow in vivo tracking and recovery of progenitor cells. Nature Biotechnology 18, 410-414 (2000).
Alivisatos, P. The use of nanocrystals in biological detection. Nature Biotechnology 22, 47-52 (2004).
Seo, W. S., Lee, J.H., Sun, X., Suzuki, Y., Mann, D., Liu, Z., Terashima, M., Yang, P.C., Micconnell, M.V., Nishimura D.G., Dai, H. FeCo/graphitic-shell nanocrystals as advanced magnetic-resonance-imaging and near-infrared agents. Nature Materials 5, 971-976 (2006).
Weissleder, R. Molecular Imaging in Cancer. Science 312, 1168-1171 (2006).
Massoud, T. F., Gambhir, S.S. Molecular imaging in living subjects: Seeing fundamental biological processes in a new light. Genes & Development 17, 545-580 (2003).
Moseley, M., Donnan, G. Multimodality Imaging: Introduction. Stroke 35, 2632-2634 (2004).
Kelly, K. A., Allport, Jr., Tsourkas, A., Shinde-Patil, V.R., Josephson, L., Weissleder, R. Detection of Vascular Adhesion Molecule-1 Expression Using a Novel Multimodal Nanoparticle. Circulation Research 96, 327-336 (2005).
Tartaj, P., Morales, M.d.P., Verdaguer, S.V., Carreno, T. G., Serna, C. G. The preparation of magnetic nanoparticles for applications in biomedicine. Journal of Physics D: Applied Physics 36, 182-197 (2003).
Kostura, L., Kraitchman, D.L., Mackay, A.M., Pittenger, M.F., Bulte, J. W. M. Feridex Labeling of mesenchymal stem cells inhibits chondrogenesis but not adipogenesis or osteogenesis. NMR in Biomedicine 17, 513-517 (2004).

(Continued)

*Primary Examiner* — Michael G Hartley
*Assistant Examiner* — Sean R Donohue
(74) *Attorney, Agent, or Firm* — Thomas|Horstemeyer, LLP

(57) ABSTRACT

Embodiments of the present disclosure provide for nanoprobes, methods of imaging, methods of imaging a target, methods of making nanoprobes, and the like.

18 Claims, 18 Drawing Sheets
(18 of 18 Drawing Sheet(s) Filed in Color)

(56) References Cited

OTHER PUBLICATIONS

Hyeon, T., Lee, S.S., Park, J., Chung, Y., Na, H. B. Synthesis of Highly Crystalline and Monodisperse Maghemite Nanocrystallites without a size-selection process. Journal of the American Chemical Society 123, 12798-12801 (2001).

Fu, A., Gu, W., Boussert, B., Koski, K., Gerion, D., Manna, L, Le Gras, M., Larabell, C. A., Alivisatos, A. P. Semiconductor Quantum Rods as Single Molecule Fluorescent Biological Labels. Nano Letters 7, 179-182 (2007).

Fu, A. , Developing new nanoprobes from semiconductor nanocrystals disertation for Ph.D. in Chemistry (University of California Berkeley, 2006).

Jun, Y.-w., Huh, Y.-m., Choi, J.S., Lee, J.H., Song, H.T., Kim, S.J., Yoon, S., Kim, K.S., Shin, J.S., Suh, J.S., Cheon, J. W. Nanoscale Size Effect of Magnetic Nanocrystals and Their Utilization for Cancer Diagnosis via Magnetic Resonance Imaging. Journal of the American Chemical Society 127, 5732-5733 (2005).

Lakowicz, J. R. Principles of Fluorescence Spectroscopy (1983 Plenum Press, New York, 1986).

Burns, A., Ow, H., Wiesner, U. Fluorescent core-shell silica nanoparticles: towards "Lab on a Particle" architectures for nanobiotechnology. Chemical Society Reviews 35, 1028-1042 (2006).

Haustein, E., Schwille, P. Ultrasensitive investigations of biological systems by fluorescence correlation spectroscopy. Methods 29, 153-166 (2003).

Magde, D., Elson, E., Webb, W.W. Thermodynamic Fluctuations in a Reacting System-Measurement by Fluorescence Correlation Spectroscopy. Physical Review Letters 29, 705-708 (1972).

Nirmal, M., Dabbousi B.O., Bawendi, M.G., Macklin, J.J., Trautman, J.K., Harris, T.D., Brus, L.E. Fluorescence Intermittency in single cadmium selenide nanocrystals. Nature 383, 802-804 (1996).

Bagshaw, C. R., Cherny, D. Blinking fluorophores: what do they tell us about protein dynamics. Biochemical Society Transactions 34, 979-982 (2006).

Rasnik, I., McKinney, S.A., Ha, T. Nonblinking and long-lasting single-molecule fluorescence imaging. Nature Methods 3, 891-893 (2006).

Min, W., English, B.P., Luo, G., Cherayil, B.J., Kou, S.C., Xie, x.S. Fluctuating Enzymes: Lessons from Single-Molecule Studies. Acc. Chem. Res. 38, 923-931 (2005).

Cui, B., Wu, C., Chen, L, Ramirez, A., Bearer, E.L., Li, W.P., Mobley, W.C., Chu, S. One at a time, live tracking of NGF axonal transport using quantum dots. Proceedings of the National Academy of Sciences of the United States of America 104, 13666-13671 (2007).

Karczmar, G. S., Fan, X., Hallaq, H.A., River, J.N., Tarlo, K., Kellar, K.E., Zamora, M., Schaeffer, C.R., Lipton, M.J. Functional and Anatomic Imaging of Tumor Vasculature: High-Resolution MR Spectroscopic Imaging Combined with a Superparamagnectic Contrast Agent. Academic Radiology 9, S115-S118 (2002).

Fu, Dissertation, Lawrence Berkeley National Lab, 2006.

Lee et al. Journal of the American Chemical Society 2006, 128, 7383-7389.

Bright and Stable Core-Shell Fluorescent Silica Nanoparticles, Nano Letters, vol. 5, No. 1, pp. 113-117, Hoooisweng OW, Daniel R. Larson, Mamta Srivastava, Barbara A. Baird, Watt W. Webb, Ulrich Wiesner, 2005.

Intracellular Spatial Control of Fluorescent Magnetic Nanoparticles, Departments of Chemistry, Biology and Physics, The Hong Kong University of Science and Technology, Clear Water Bay, Hong Kong, China, Jinjao Gao, Wei Zhang, Pingbo Huang, Bei Zhang, Xixiang Zhang, Bing Xu.

Silica- and Alkoxysilane-Coated Ultrasmall Superparamagnetic Iran Oxide Particles: A promising Tool to Label Cells for Magnetic Resonance Imaging, Chungfu Zhang, Bjorn Wangler, Bernd Morgenstern, Hanswalter Zentgraf, Michael Eisenhut, Harald Untenecker, Ralf Kruger, Ralf Huss, Christian Selger, Wolfhard Semmler, Fabian Kiessling, 2007.

Biosensing Using Porous Silicon Double-Layer Interferometers: Reflective Interferometric Fourier Transform Spectroscopy, Claudia Pacholsky, Marta Sartor, Michael J. Sailor, Frederique Cunin Gordon M. Miskelly, 2005.

Quantum Dot and Multifunctional Nanoparticles: New Contrast Agents for Tumor Imaging, Matthew N. Rhyner, Ander M. Smith, Xiaohu Gao, Hui Mao, Lily Yang, Shuming Nie, 2006.

Designing Quantum-Dot Probes, Rumiana Bakalova, Zhivko Zhelev, Ichio Aoki, Iwao Kanno, Nature Photonics, vol. 1, Sep. 2007.

Optical Tracking and Detection of Immunomagnetically Selected and Aligned Cells, Arjan G.J. Tibbe, Bart G. de Grooth, Jan Greve, Paul A. Liberti, Gerald J. Dolan, Leon W.M.M. Terstappen, Nature Biotechnology, vol. 17, Dec. 1999.

Optical and MRI Multifunctional Nanoprobe for Targeting Gliomas; OMID Veiseh, Conroy Sun, Jonathan Gunn, Nathan Kohler, Patrick Gabikian, Donghoon Lee, Narayan Bhatiarai, Richard Ellenbogen, Raymond Sze, Andrew Hallahan, Jim Olson, Miqin Zhang; 2005 American Chemical Society.

Characterization of Photoinduced Isomerization and Back-Isomerization of Cyanine Dye Cy5 by Fluorescence Correlation Spectroscopy; Jerker Widengren, Petra Schwille; Department of Spectroscopy and Photochemical Kinetics, and Department of Experimental Biophysics, Max-Planck Institute for Biophyiscal Chemistry 370 77 Gottingen, Germany; 200 American Chemical Society, 2000.

Artiicially Engineered Magnetic Nanoparticles for Ultra-Sensitive Molecular Imagin; Jae-Hyun Lee, Yong-Min Huh, Young-Wookjun, Jung-Wook Seo, Jung-Tak Jang, Ho-Taek Song, Sungjun Kin, Eun-Jun Cho, Ho-Geun Yoon, Jun-Suck Suh, Jinwood Cheon; Nature Medicine, vol. 13, No. 1, Jan. 2007.

Dye-Labeled Poly (organosiloxane) Microgels with Core-Shell Architecture; Christina Graf, Wolfgang Schartl, Karl Fischer, Norbert Hugenberg, Manfred Schmidt; Institut fur Physikalische Chemie der Universitat Mainz, Welderweg 11, 55099 Mainz, Germany; 1999 American Chemical Society.

A Multimodal Nanoparticle for Preoperative Magnetic Resonance Imaging and Intraoperative Optical Brain Tumor Delineation; Mortiz F. Kircher, Umar Mahmood, Raymond S. King, Ralph Weissleder, Lee Josephson; Center for Molecular Imaging Research, Massachusetts General Hospital and Harvard Medical School, Charlestown, Massachusetts; Cancer Research 63, 8122-8125, Dec. 1, 2003.

Epithelial Internalization of Superparamagnetic Nanoparticles and Response to External Magnetic Filed; Kenneth Dormer, Charles Seeney, Kevin Lewelling, Guoda Lian, Donald Gibson, Matthew Johnson; Department of Physiology, Oklahoma University Health Sciences Center, Chemistry Department, NanoBioMagnetics, Inc., Physics Department, Oklahoma Christian University, Department of Physics and Astronomy, University of Oklahoma; 2004.

Multimodality Molecular Imaging Identifies Proteolytic and Osteogenic Activities in Early Aortic Valve Disease, Circulation Journal of the American Heart Association; Elena Aikawa, Matthias Nahrendorf, David Sosnovik, Vicent M, Lok, Farouc A. Jaffer, Masanori Aikawa, Ralph Weissleder; Circulation 2007; Jan. 15, 2007.

Visual Recognition and Efficient Isolation of Apoptotic Cells wtih Fluorescent-Magnetic-Biotargeting Multifunctional Nanospheres; Er-Qun Song, Guo-Ping Wang, Hai-Yan Xie, Zhi-Ling Zhang, Jun Hu, Jun Peng, Dao-Cheng Wu, Yun-Bo Shi, Dai-Wen Pang; 2007 American Association for Clinical Chemistry.

Fluorescence-Modified Superparamagnetic Nanoparticles: Intracellular Uptake and Use in Cellular Imaging; Frank Bertorelle, Claire Wilhelm, Jacky Roger, Florence Gazeau, Christine Menager, Valerie Cabuil; 2006 American Chemical Society.

Superparamagnetic Iron Oxide Nanoparticle Probes for Molecular Imaging; Daniel L. J Thorek, Anthony K. Chen, Julie Czupryna, Andrew Tsourkas; Published in Annal's of Biomedical Engineering, vol. 34, Issue 1, Jan. 2006

Physical and Chemical Properties of Superparamagnetic Iron Oxide MR Contrast Agents: Ferumoxides, Gerumoxtran, Ferumoxsil; Chu W. Jung, Paul Jacobs; Advanced Magnetics, Inc., Cambridge, MA 02138-1038, USA 1995.

(56) References Cited

OTHER PUBLICATIONS

Synthesis and Characterization of Multi-Functional Nanoparticles Possessing Magnetic, Up-Conversion Fluorescence and Bio-Affinity Properties; Huachang Lu, Guangshun Yi, Shuying Zhao, Depu Chen, Liang-Hong Guo, Jing Cheng; J. Mater. Chem., 2004, 14, 1336-1341; Department of Chemistry, China; National Research Engineering Chenter for Beijing Biochip Technology, China; School of Materials Schience & Engineerin, Shandong University ofTechnoloy, China; Department of Biological Sciences, China.

Simultaneous in vivo Positron Emission Tomography and Magnetic Resonance Imaging; Ciprian Cat Ana; Daniel Procissi, Yibao Wu, Martins. Judenhoffer, Jinyi Qi, Bernd J. Pichler, Russell E. Jacobs, Simon R. Cherry; Department of Biomedical Engineering, University of California, Genome and Biomdeical Sciences Facility, Beckman Institute, California Institute of Technology, Department of Radiology, Laboratory for Preclinical Imaging and Imaging Technology, University of Tubingen, Germany, 2008.

Quantum Dots with a Paramagnetic Coatign as a Bimodal Molecular Imaging Probe—NANO Letters; William J. M. Mulder, Rolf Koole, Ricardo J. Brandwijk Gert Storm, Patrick T.K. Chin, Gustav J. Strijkers, Celos de Mello Donega, Klaas Nicolay, Arjan W. Griffioen; Biomedical NMR, Department of Biomedical Engineering, Eindhoven University ofTechnology, Debye Institute, Angiogenesis Laboratory, Utrecht Institute for Pharmaceutical Sciences, Laboratory of Macromolecular and Organic Chemistry, The Netherlands, 2006.

Multifunctional Inorganic Nanoparticles for Imaging, Targeting, and Drug Deliver; Monty Liong, Jie Lu, Michael Kovochich, Tian Xia, Stefan G. Ruehm, Andre E. Nel, Fuyuhiko Tamanoi, Jeffrey I. Zink; Department of Chemistry and Biochemistry, Department of Microbiology, Immunology, and Molecular Genetics, Department of Medicine, and Department of Radiological Sciences, University of California, Los Angeles, California; vol. 2, No. 5, 889-896, 2008.

Multifuncational Polymeric Micelles as Cancer-Targeted, MRI-Ultrasensitive Drug Delivery System; Norased Nasongkla, Erik Bey, Jimin Ren, Hua Ai, Chalermchai Khemtong, Jagadeesh Setti Gunthi, Shook-Fong Chin, A. Dean Sherry, David A. Boothman, Jinming Gao; Advanced Imaging Research Center, Simmons Comprehensive Cancer Center, University of Texas Southwestern Medical Center at Dallas, NANO Letters, vol. 0, No. 0 A-D, 2006.

\* cited by examiner

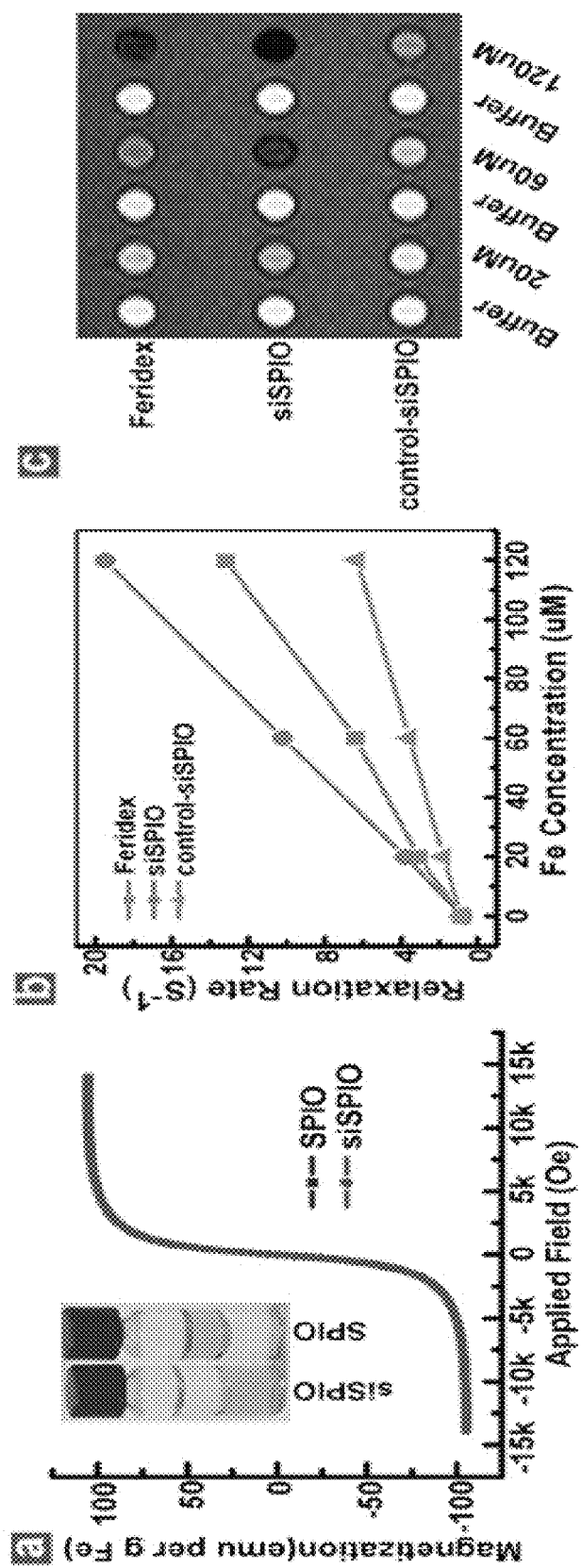
FIG. 1.1

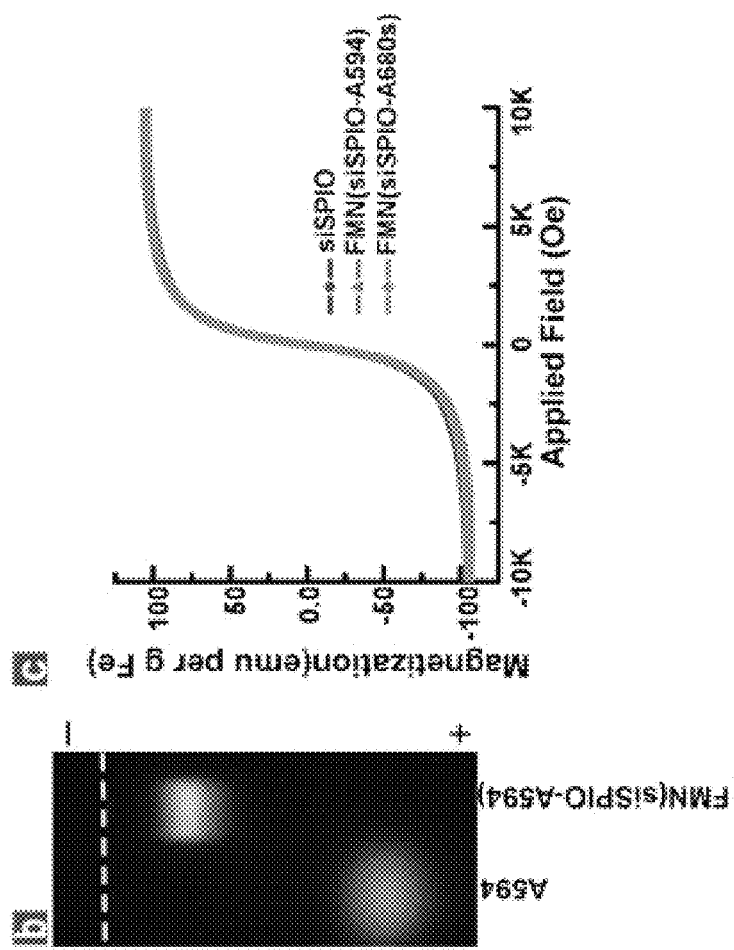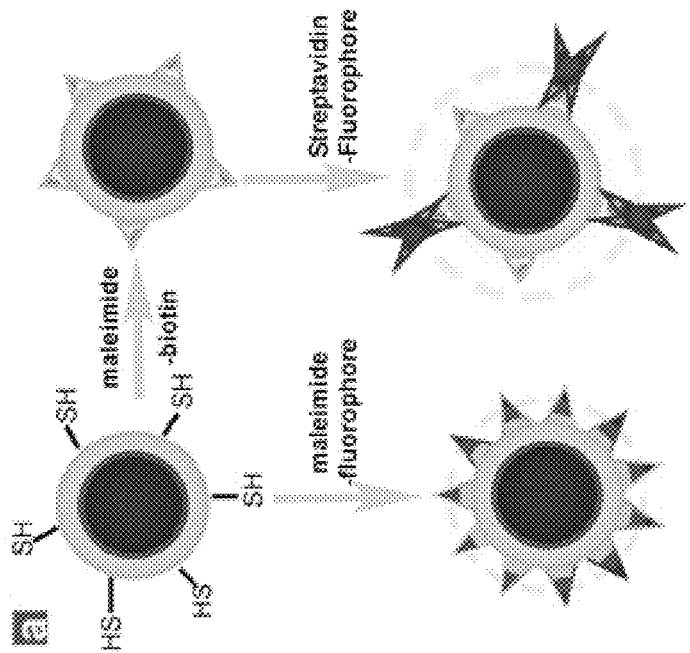
FIG. 1.2

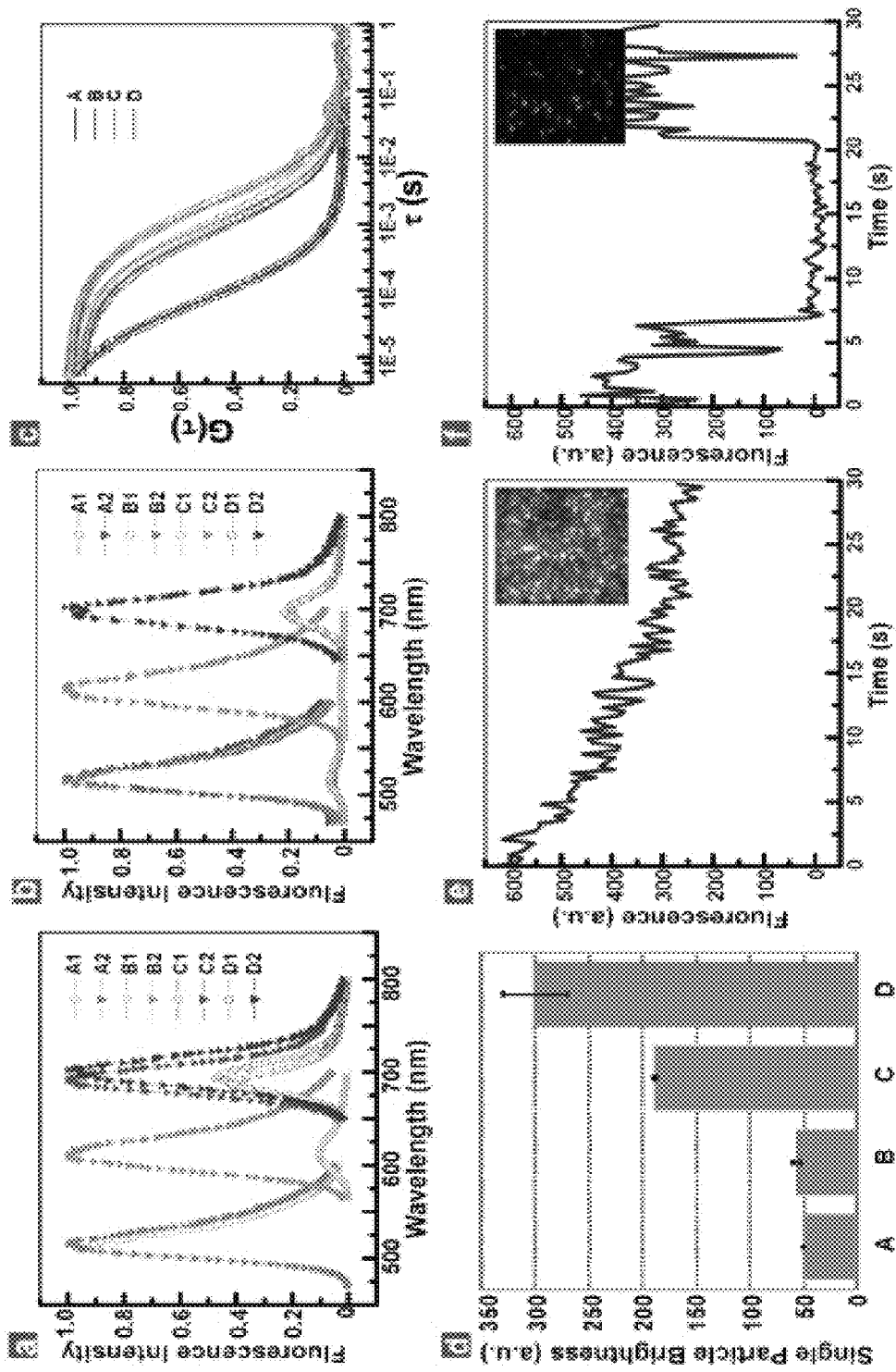
FIG. 1.3

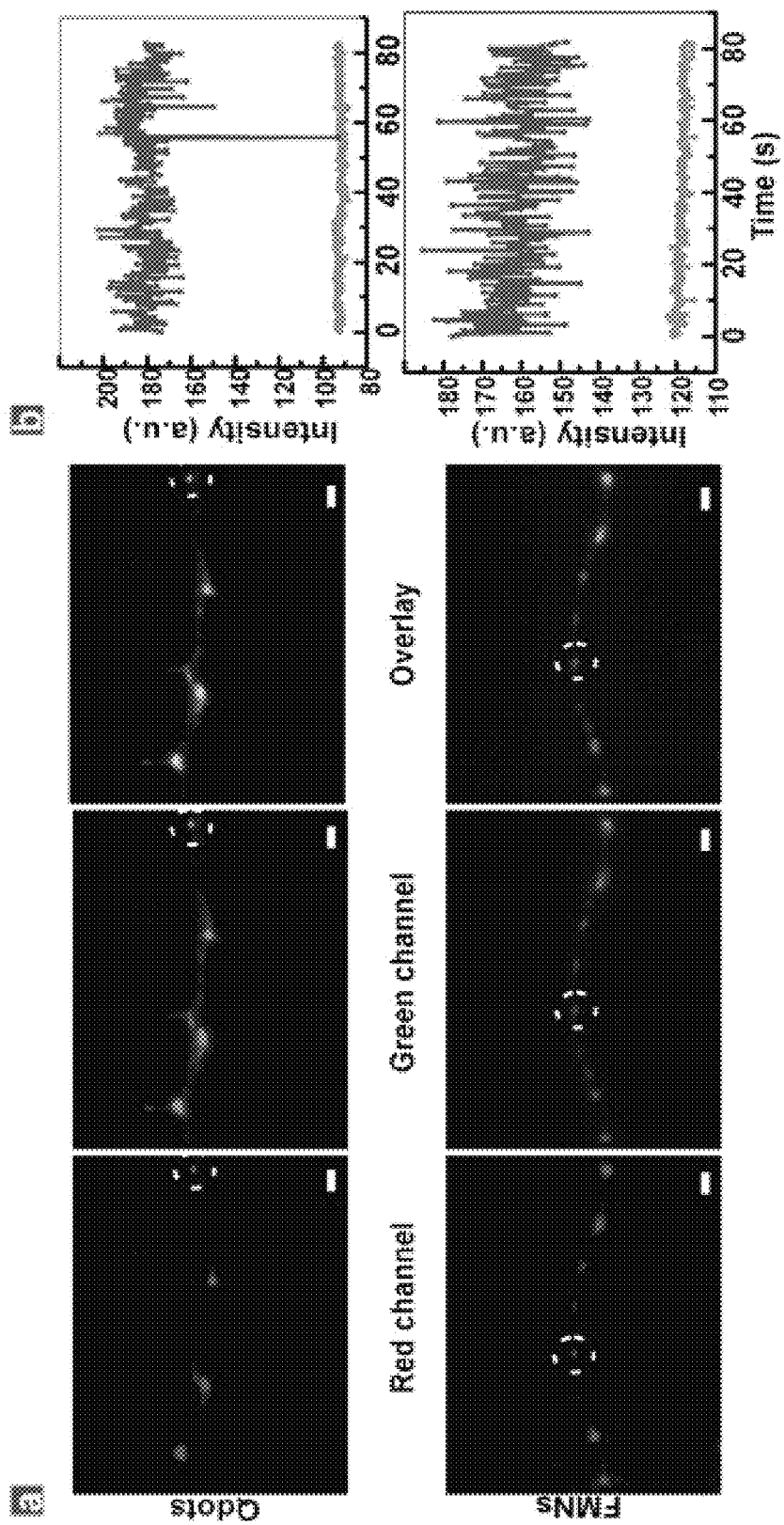
FIG. 1.4

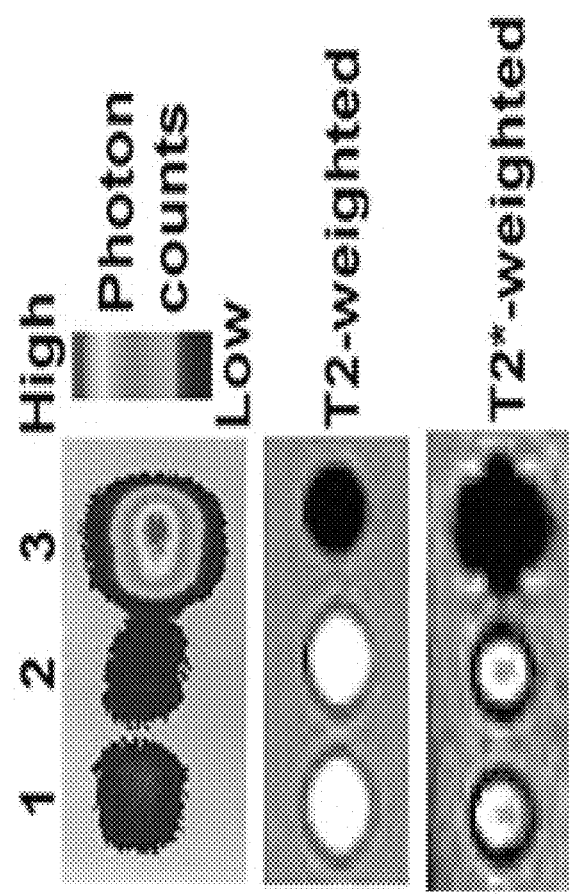
FIG. 1.5

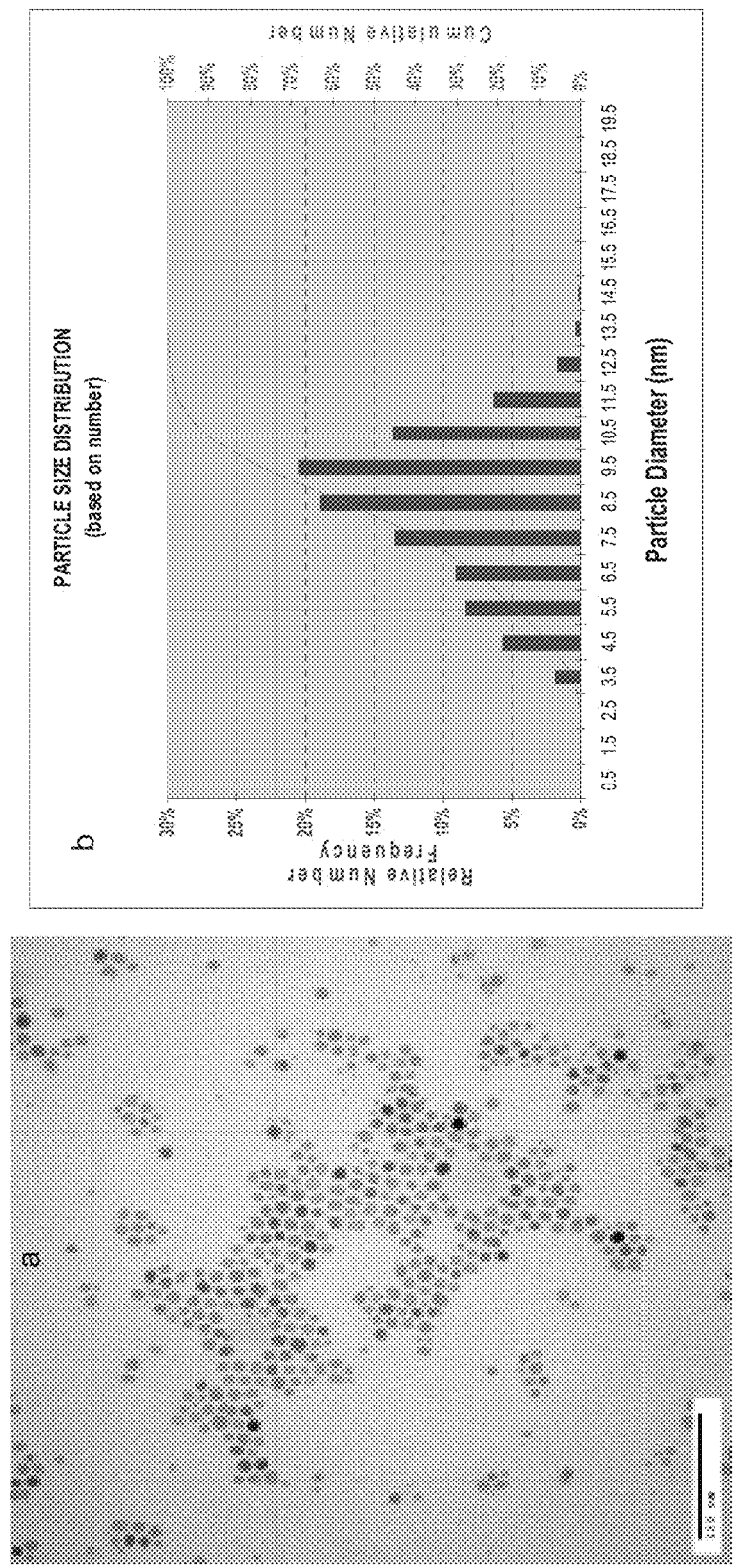
FIG. 1.6

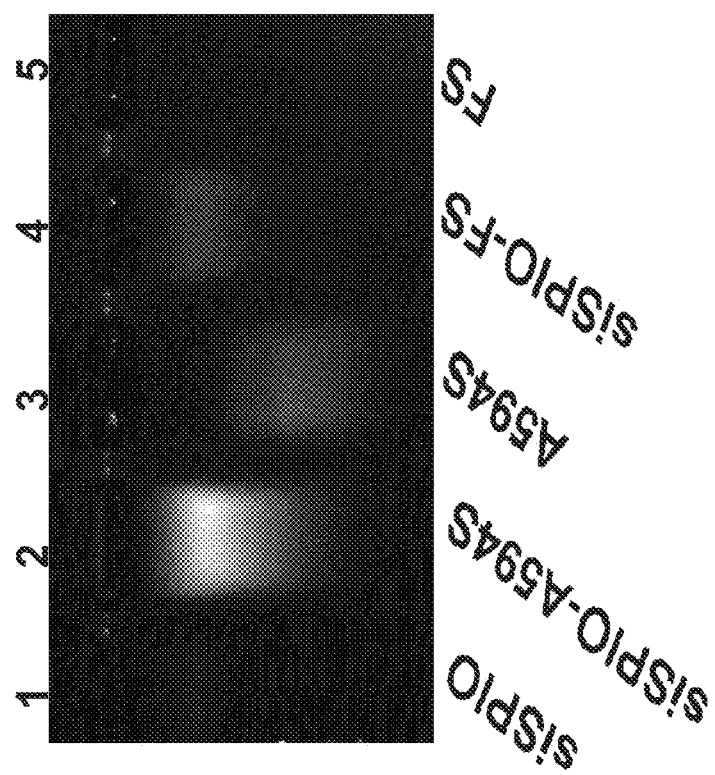
FIG. 1.7

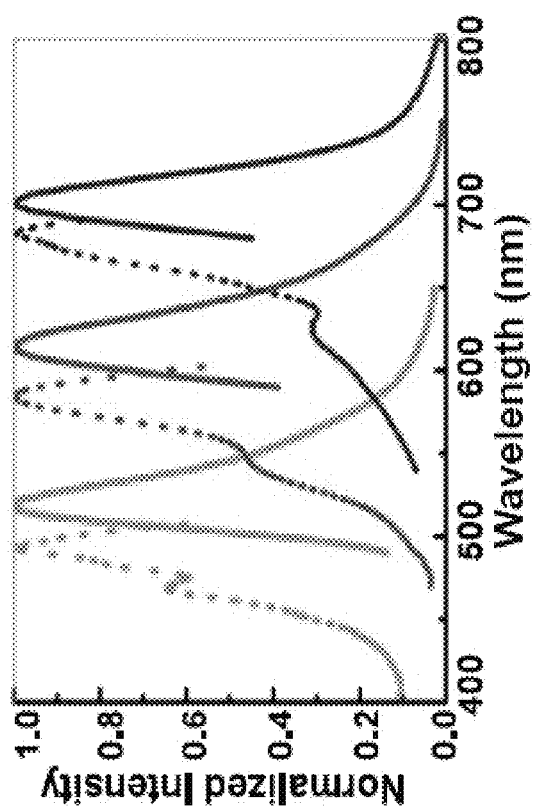
FIG. 1.8

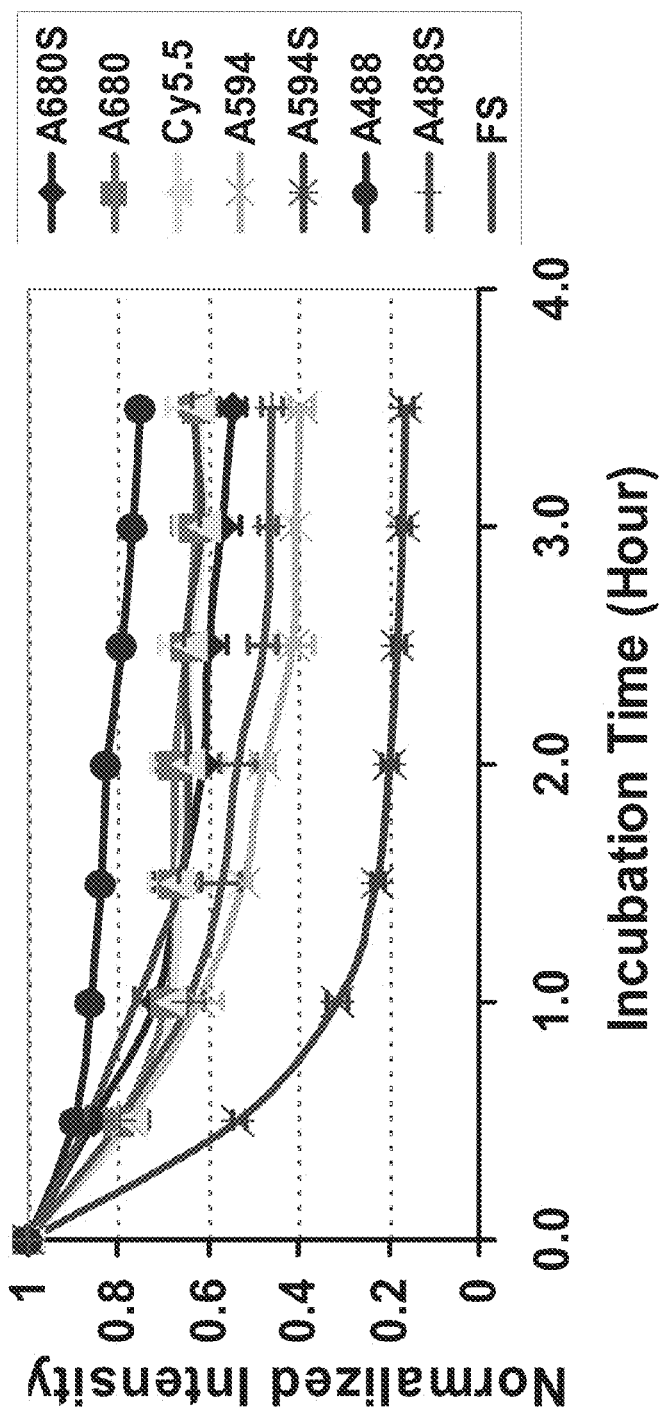
FIG. 1.9

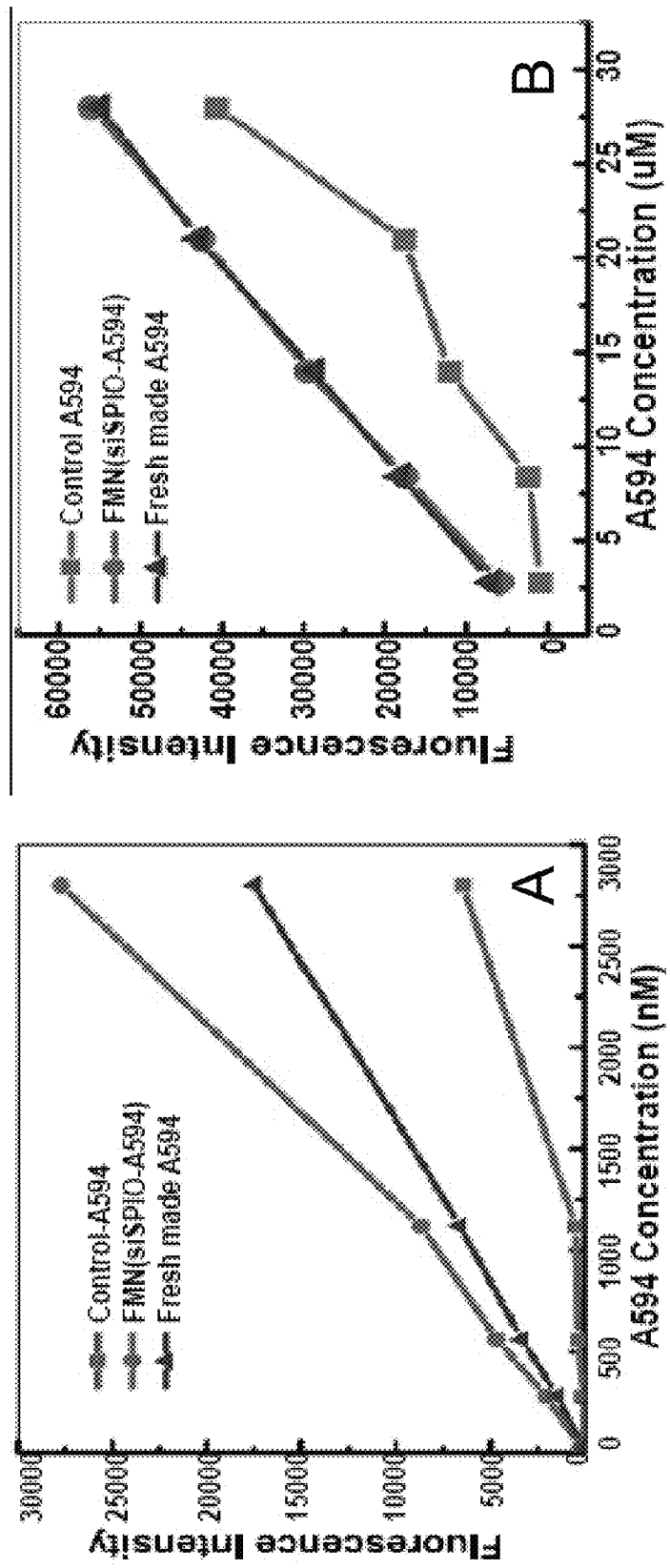
FIG. 1.10

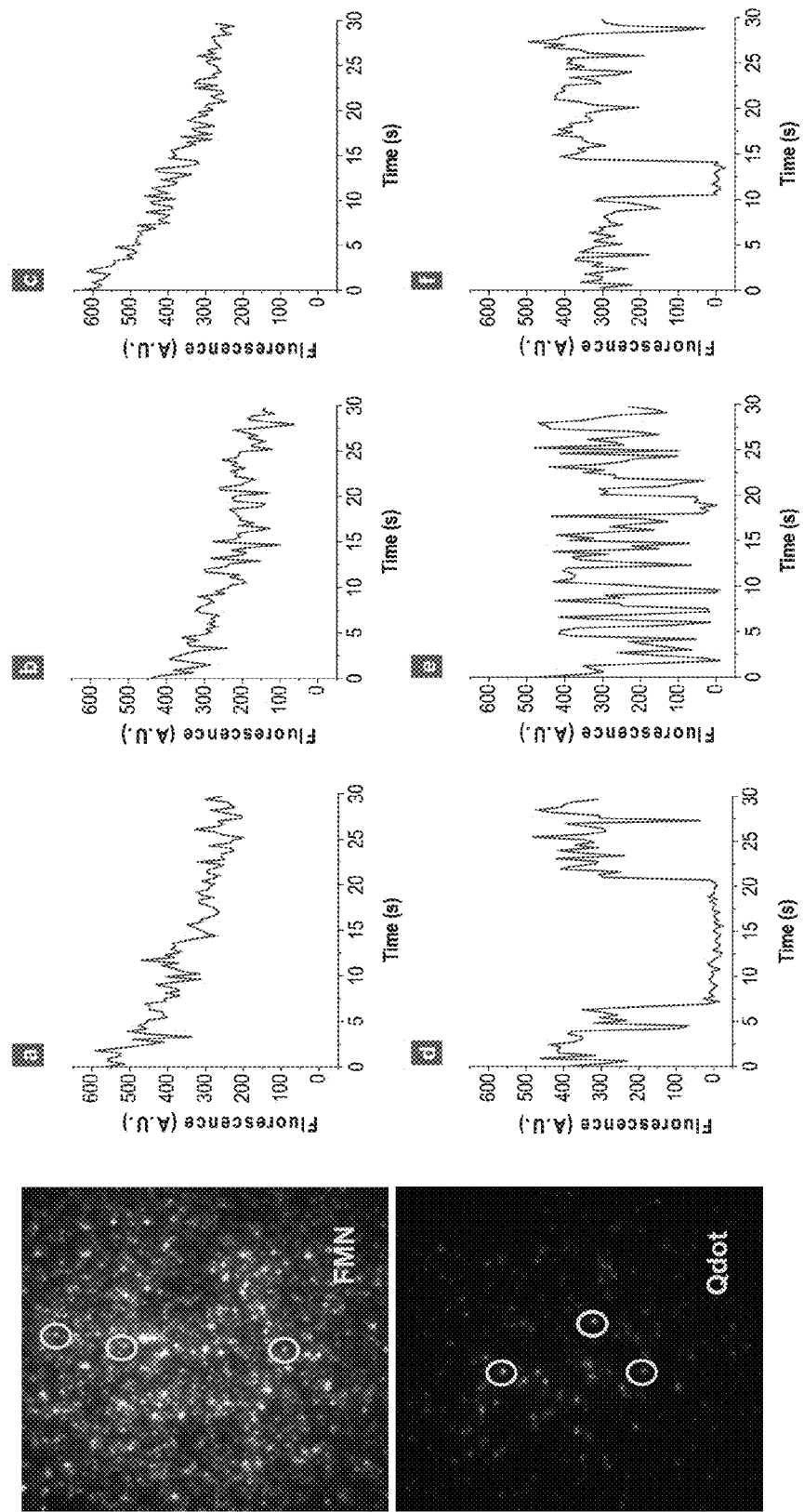
FIG. 1.11

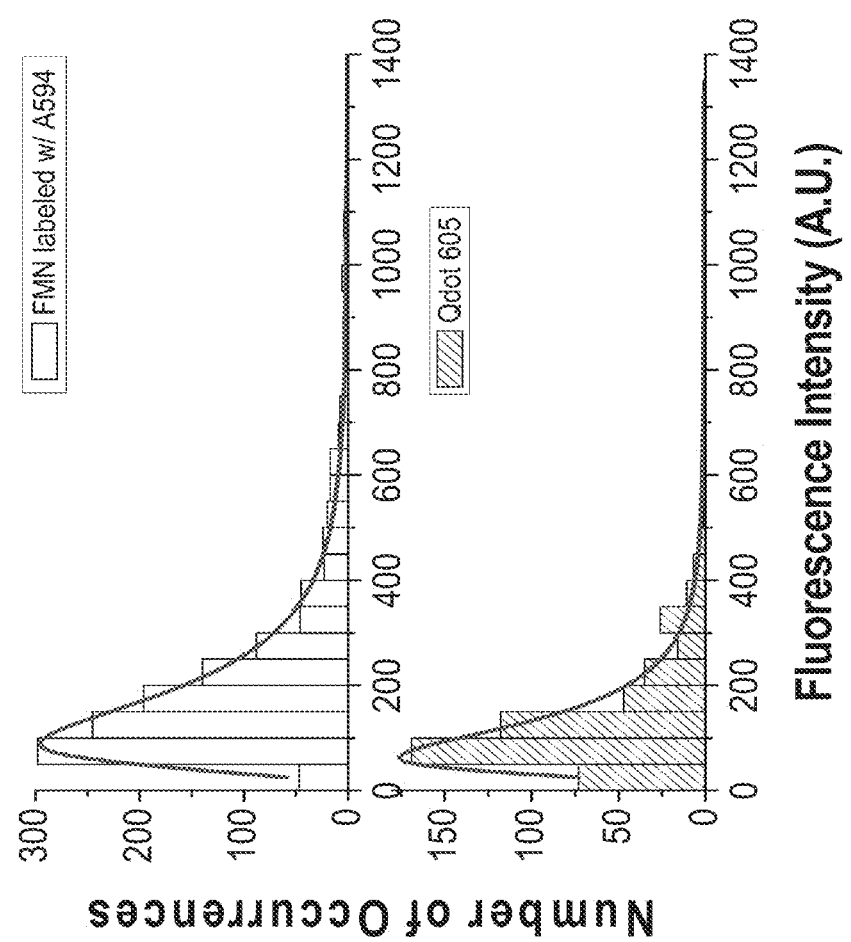
FIG. 1.12

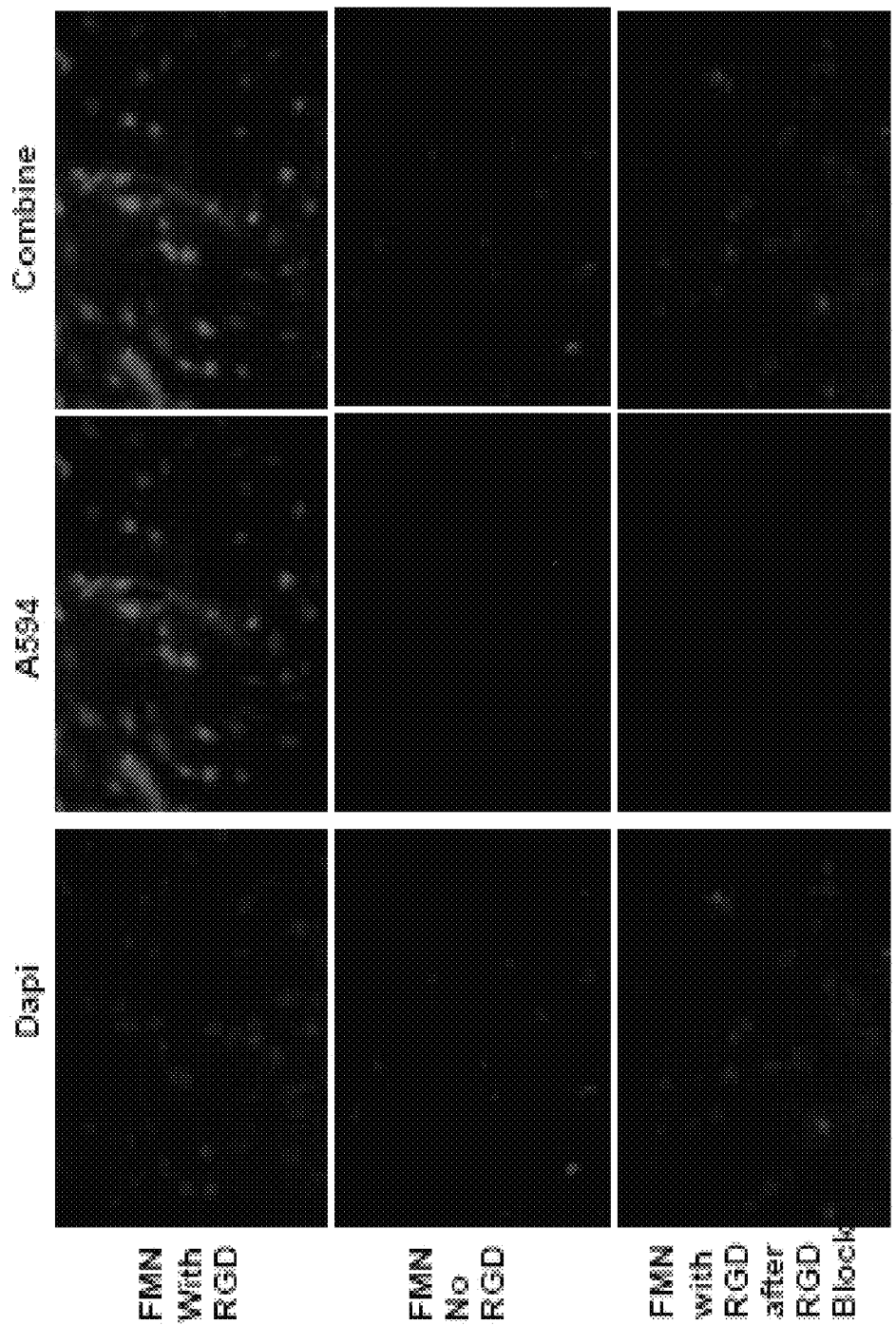
FIG. 2.1

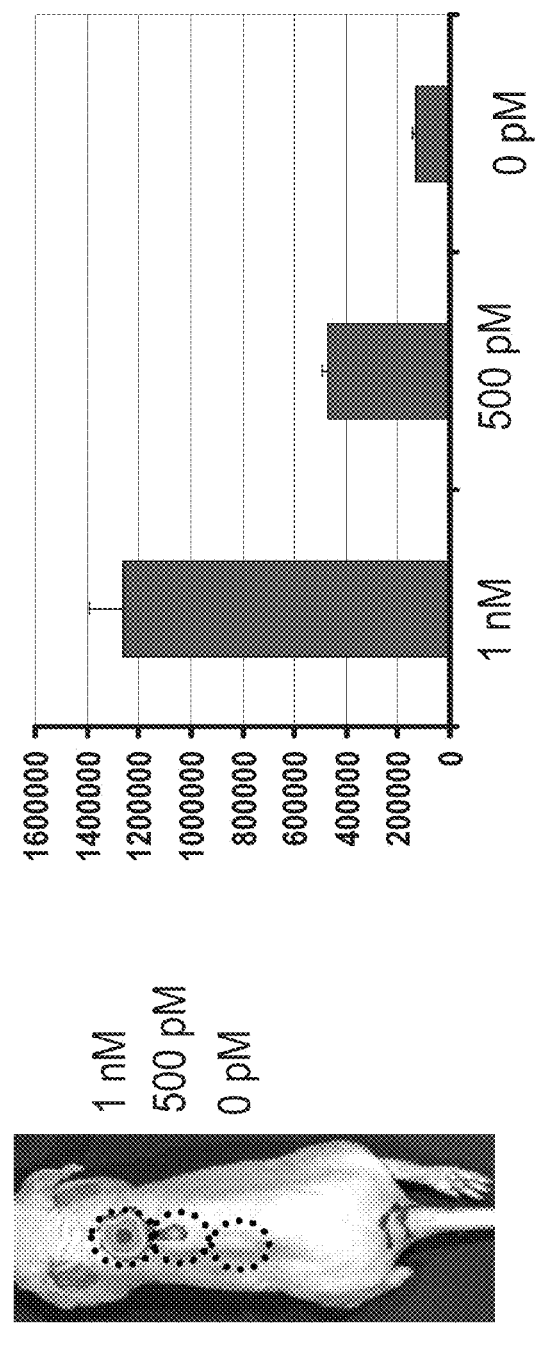
FIG. 2.2
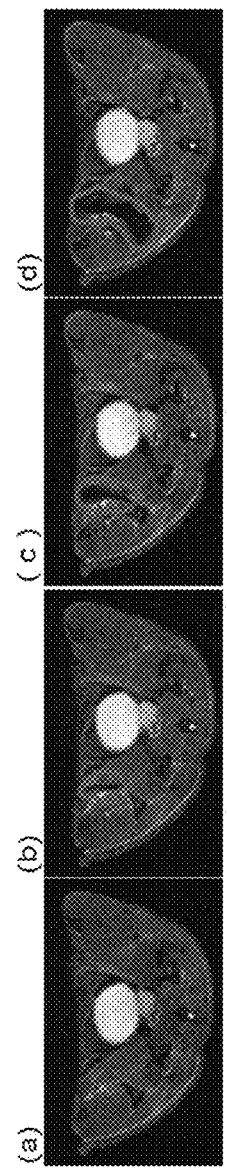
FIG. 2.3

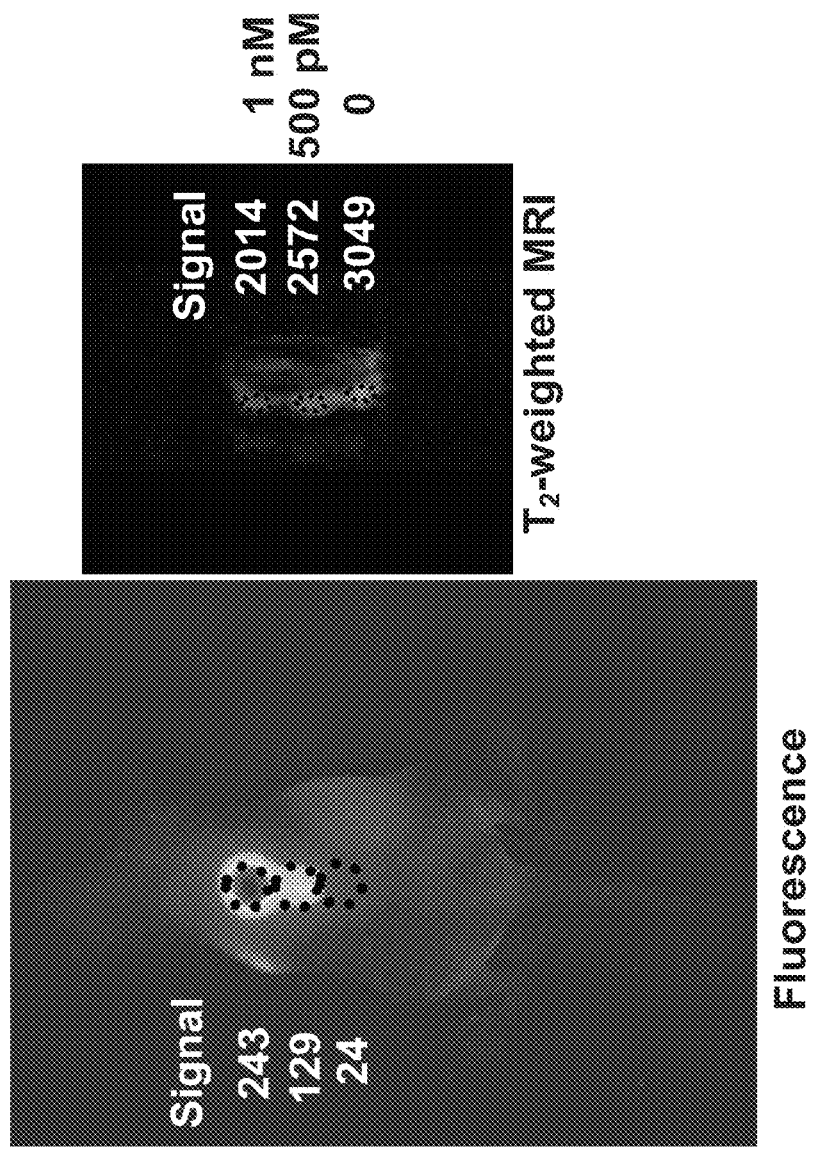
FIG. 2.4

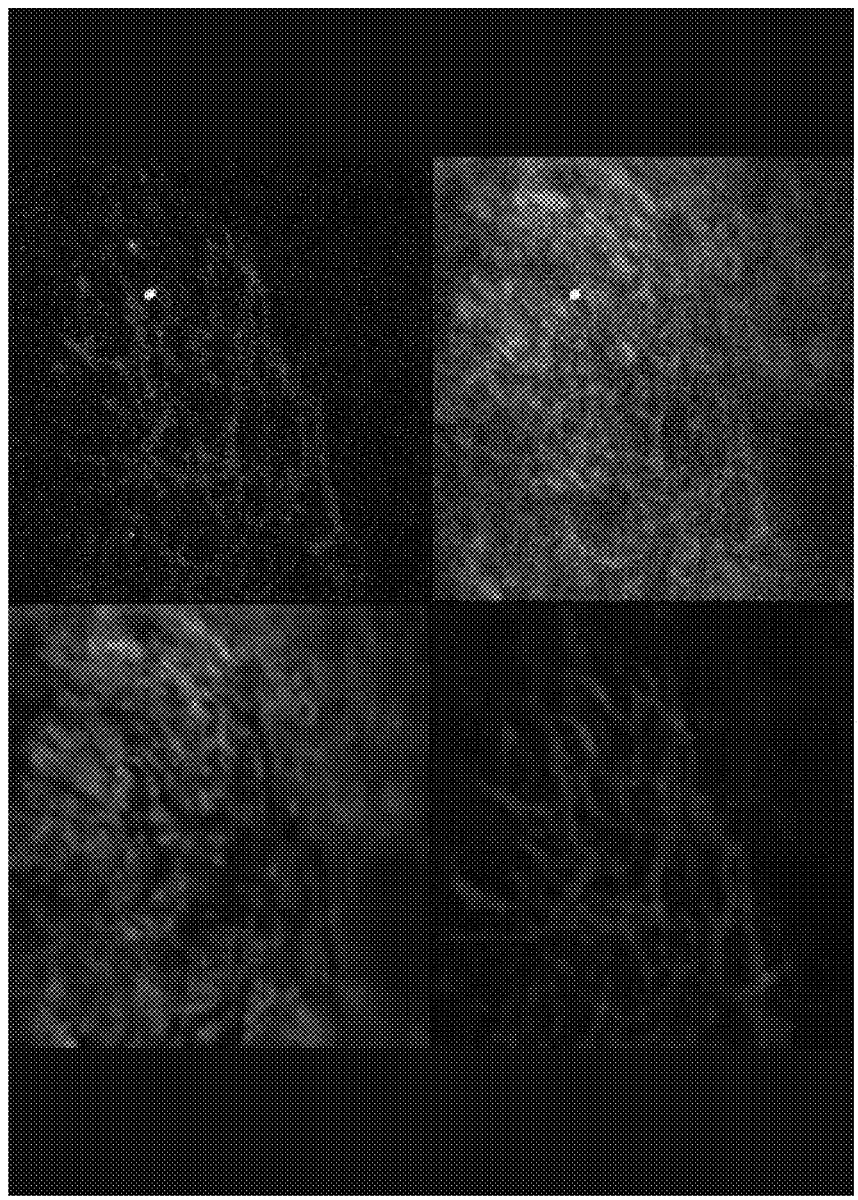
FIG. 2.5

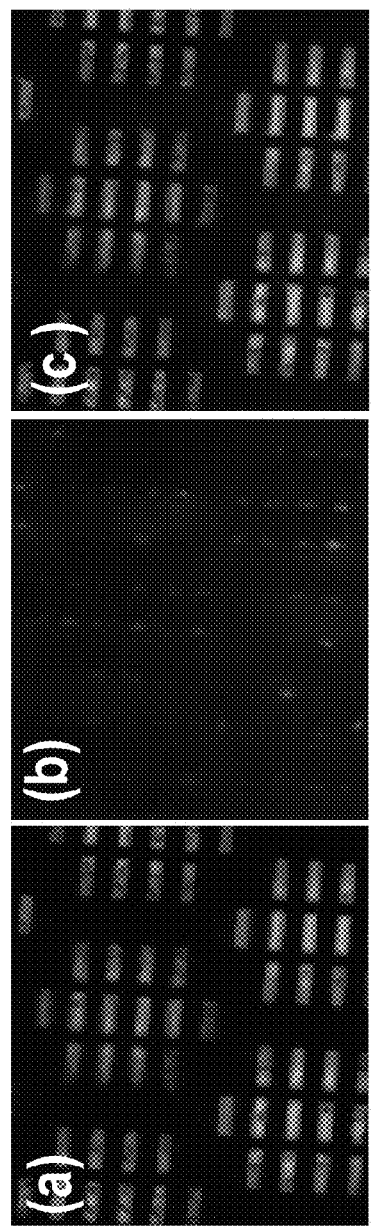
FIG. 2.6

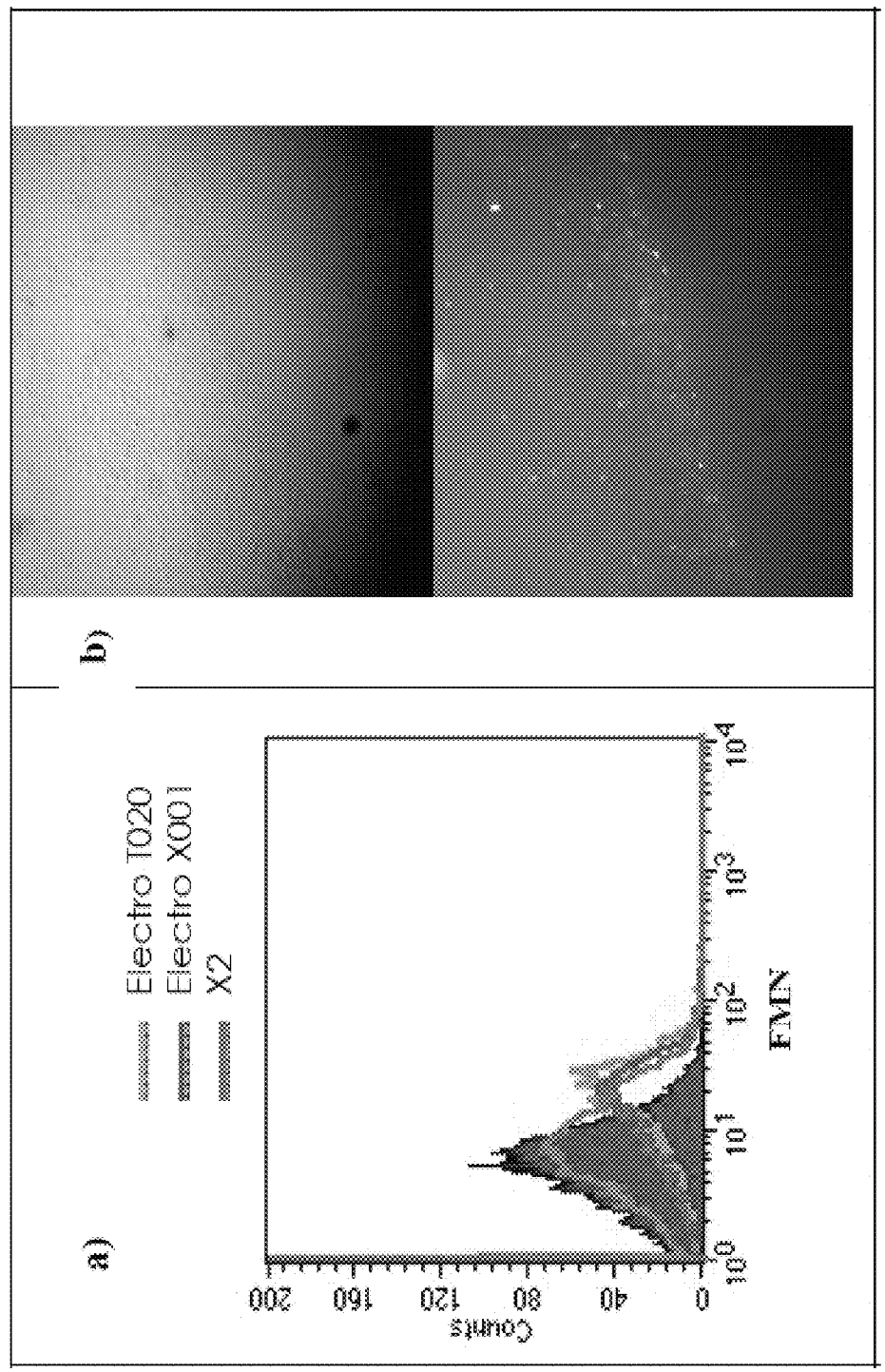
FIG. 2.7

FLUORESCENT MAGNETIC NANOPROBES, METHODS OF MAKING, AND METHODS OF USE

CROSS-REFERENCE TO RELATED APPLICATIONS

This application is a continuation of U.S. non-provisional application entitled "FLUORESCENT MAGNETIC NANOPROBES, METHODS OF MAKING, AND METHODS OF USE," having Ser. No. 12/460,007 filed on Jul. 10, 2009 and claims priority to U.S. provisional application entitled, "FLUORESCENT MAGNETIC NANOPROBES, METHODS OF MAKING, AND METHODS OF USE," having Ser. No. 61/079,485, filed on Jul. 10, 2008, which are entirely incorporated herein by reference.

FEDERAL SPONSORSHIP

This invention was made with Government support under contracts CA119367 and EB008558 awarded by the National Institutes of Health. The Government has certain rights in this invention.

BACKGROUND

The fabrication of high performance nanoscale materials useful for ultra sensitive molecular imaging, early stage diagnosis and targeted therapy is of great interest.[1-4] Smart nanomaterials that can integrate different properties and functionalities are especially desirable.[4,5] For example, nanomaterials that combine the complementary features of magnetic resonance imaging (MRI) and optical imaging could lead to significant technological advantages for molecular imaging and diagnostics, since MRI provides exquisite spatial-resolution and anatomical contrast, while optical imaging is highly sensitive, less costly, and easier to implement.[4,6-9] Pioneering studies have demonstrated clear synergies between these two imaging modalities, however, the magnetic and optical properties of the underlying nanomaterials are still far from optimal.[10-12] In addition, none of the reported magnetic and optical nanomaterials have shown advantageous imaging capabilities at the single molecule level.

SUMMARY

Embodiments of the present disclosure provide for nanoprobes, methods of imaging, methods of imaging a target, methods of making nanoprobes, and the like.

One exemplary nanoprobe, among others, includes: a superparamagnetic iron oxide (SPIO) nanoparticle, wherein the SPIO nanoparticle has a silanization coating on the surface of the SPIO nanoparticle; and at least one fluorescent compound attached to the silanization coating.

One exemplary method of imaging, among others, includes: administering one or more of the coated SPIO nanoparticles described herein; and detecting an energy from the coated SPIO nanoparticle in the host.

One exemplary method of imaging a target, among others, includes: administering one or more of the coated SPIO nanoparticles described herein, wherein the SPIO includes a targeting moiety, wherein the targeting moiety has an affinity for the target; and detecting an energy from the coated SPIO nanoparticle in the host, wherein the location of the energy indicates the location of the target.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 1.1a-c illustrate the magnetic property, solubility and MRI capability of siSPIO in comparison with related samples. FIG. 1.1a illustrates room temperature magnetization versus applied field data for SPIO in toluene (A, blue curve) and siSPIO (B, red curve) in PBS. Inset shows the solubility of siSPIO (left) and the original SPIO (right) in PBS (bottom layer) and Toluene (top layer). FIG. 1.1b illustrates MR transverse relaxation rate ($T_2^{-1}$) versus Fe concentration for siSPIO (green color), control-siSPIO (red color), and Feridex solutions (yellowish green color). The MR transverse relaxivity values of each sample were obtained from the linear fits of experimental $T_2^{-1}$ vs. Fe concentration data. FIG. 1.1c illustrates MR images of siSPIO, control-SPIO and Feridex at three metal concentrations obtained using a T2-weighted spin-echo sequence with TR of 2,000 ms and TE of 160 ms.

FIGS. 1.2a-c illustrate fluorescent magnetic nanoprobes (FMNs). FIG. 1.2a is a schematic illustration of two methods to make siSPIO into FMNs. siSPIO with surface mercapto groups is used in the illustration. FIG. 1.2b illustrates a gel-electrophoresis image showing the migration of FMN made of siSPIO and A594 (right lane) is retarded compared to free A594 (left lane), proving the success of the fluorophore incorporation. FIG. 1.2c illustrates a room temperature magnetization versus applied field data for siSPIO (red curve), FMN made of siSPIO and A594 (green curve), and FMN made of siSPIO and A680S (wine curve). The incorporation of fluorophores to siSPIO to make FMN does not alter the magnetic properties of siSPIO, as demonstrated by the overlapping magnetization curves and the same Ms.

FIGS. 1.3a-f illustrate the fluorescence property characterization of fluorescent magnetic nanoprobes (FMNs). FIG. 1.3a illustrates a fluorescence emission spectra of FMNs (with fluorophores directly conjugated to the FMN surface) in comparison with free fluorophores at the same fluorophore concentration of 300 nM. A2, FMNs with A488, A2, control A488; B1, FMNs with A594, B2, control A594; C1, FMNs with Cy5.5, C2, control Cy5.5; D1, FMNs with A680, D2, control A680. FIG. 1.3b illustrates a fluorescence emission spectra of FMNs (with streptavidin-fluorophores conjugated to the FMNs surface using the streptavidin-biotin linkage) in comparison with unincorporated streptavidin-fluorophores at the same fluorophore concentration of 300 nM. A1, FMNs with Fs, A2, control Fs; B1, FMNs with A488s, B2, control A488s; C1, FMNs with A594s, C2, control A594s; D1, FMNs with A680s, D2, control A680s. FIG. 1.3c illustrates FCS curves. A, free A594; B, FMNs with less A594 incorporated (reaction ratio of siSPIO:A594=1:50, purified sample); C, Qdot®605; D, FMNs with more A594 incorporated (reaction ratio of siSPIO:A594=1:500, purified sample). All curves are fitted by 1-species 3D diffusion model. The obtained diffusion coefficients are $3.6 \times 10^{-6}$, $3.2 \times 10^{-7}$, $2.5 \times 10^{-7}$ and $1.3 \times 10^{-7}$ cm²/s, respectively. FIG. 1.3d illustrates a single particle brightness for the same set of samples as in FIG. 3c is 49, 55, 188, and 300 for the sample A, B, C, and D, respectively. The single particle brightness of the FMN (D) exceeds that of the Qdot (C). FIGS. 1.3e and 1.3f illustrate representative single particle fluorescence intensity traces of FMNs (sample D as in FIGS. 1.3c and 1.3d) and Qdots (sample C as in FIGS. 1.3c and 1.3d), respectively. The same excitation laser power (2.3 mW) was used for both FIGS. 1.3e and 1.3f. The insets show the first frames of the fluorescence video images.

FIGS. 1.4a and 1.4b illustrate the comparison of FMNs and Qdots for single molecule fluorescence imaging experiments. FIG. 1.4a illustrates imaging and tracking of Qdots and FMNs labeled surface synaptotagmin (red spots) on rat hippocampal CA3-CA1 neurons. Green channel images show the presynaptic boutons, punctate like structures marked by synaptophysin-EGFP. Scales bars are corresponding to 2 μm. FIG. 1.4b illustrates the single particle fluorescence intensity traces of a Qdot-labeled and a FNN-labeled synaptotagmin. The Qdot and the FMN are circled in FIG. 1.4a.

FIG. 1.5 illustrates fluorescent magnetic nanoprobes (FMN) for NIR fluorescence and magnetic resonance imaging. Sample 1, Control-A680s that was freshly prepared immediately before running the gel-electrophoresis; Sample 2, Control-A680s that went through overnight PBS incubation; and Sample 3, FMN made with siSPIO-biotin and A680s, also incubated in PBS overnight as 2. All samples have the same A680s concentration. The FMN sample shows much stronger NIR fluorescence compared with free fluorophore control samples (top panel) and also shows enhanced imaging contrast for both T2 (middle panel) and T2* (bottom panel) weighted MRI images.

FIG. 1.6a illustrates a digital image of SPIO nanoparticles and FIG. 1.6b illustrates a digital image particle size distribution from TEM image analysis. The mean diameter of particle is 8.4 nm, standard deviation is 2.1 nm; particles counted was 3347.

FIG. 1.7 illustrates a gel-electrophoresis image of siSPIO, FMNs of siSPIO labeled with streptavidin conjugated fluorophores, and free streptavidin conjugated fluorophores. The electrophoresis migration of free streptavidin conjugated fluorophores is slower compared with corresponding FMN samples. Sample loading amount and streptavidin conjugated fluorophore concentration are the same for lane 2 and 3 (A594s), lane 4 and 5 (Fs). Lane 2 and lane 4 show stronger fluorescent brightness because of the fluorescence stabilization effect from siSPIO for incorporated fluorophores.

FIG. 1.8 illustrates the excitation and emission spectra showing FMNs with excellent tunability of fluorescence wavelengths. Simply by incorporating fluorophores with different absorption and emission wavelengths (green: FMNs with Fs, red: FMNs with A594s, brown: FMNs with A680s), FMNs with different excitation and emission profiles were made.

FIG. 1.9 illustrates the instability of fluorescence signal of various fluorophores. For all samples, the fluorophore concentrations were 300 nM as determined by Uv-vis spectrophotometry using the peak absorbances and the corresponding extinction coefficients. All samples were freshly made into a PBS solution (10 mM PB, 100 mM NaCl) of 200 μl. For each fluorophore, 3 samples were prepared and measured the same time for the statistical analysis. The measurement was performed using a TECAN plate reader with the following parameters: the excitation wavelength was set at 450 nm for A488, A488s and Fs, at 545 nm for A594 and A594s, and at 630 nm for A680s, A680 and Cy5.5; the emission wavelength was set at 515 nm for A488, A488s and Fs, at 615 nm for A594 and A594s, and at 700 nm for A680s, A680 and Cy5.5. And for all of the measurements, the bandwidths of emission and excitation were 12 nm; the integration time was 50 μs; the gain was 100.

FIGS. 1.10a and 1.10b illustrate the fluorescence stabilization effects of FMNs. In all samples, the concentration of siSPIO was 28 nM. A594 was with maleimide modification and was attached to siSPIO through maleimide-thiol reaction to make FMNs. To prepare the sample, we used stock solutions of 150 nM of siSPIO in PB and 1.1 mM A594 (by dissolving the 1 mg commercial sample into 1000 ul H2O and calculating the concentration with Mass/Molar Mass/Volume). All sample volume was adjusted to 150 μl using PB. And all samples were with a NaCl concentration of 100 mM. Control A594 and the corresponding FMN samples went through the same preparation and overnight incubation except that for control A594 samples, PB solution was added instead of the siSPIO solution. The fresh made A594 was prepared on the second day immediately before the fluorescence intensity measurement with a TECAN microplate reader. In FIG. 1.10a, FMN samples have slightly higher intensities than fresh made A594. This may simply be due to random errors involved in experimental preparation like pipetting error and inhomogeneous mixing of a solution, because the sample preparation involves multiple dilution of the fluorophore stock solution including at small volume scale (1 μl). In addition, the lag time between the sample preparation and the TECAN measurement could also contribute to the difference, since the fluorescence of a freshly made fluorophore solution decreases with time (FIG. 1.8). For the measurement of the fluorophore samples with high concentration (right graph), less gain was applied to avoid fluorescence intensity saturation from the measurement using the TECAN microplate reader. So the absolute intensity values between the FIGS. 1.10a and 1.10b should not be compared.

FIGS. 1.11a to 1.11f illustrate single particle fluorescence intensity traces of FMNs labeled with A594 (FIGS. 1.11a-c) and Qdots 605 (FIGS. 1.11d-f). The fluorescence images (on the left) of the first frames of the videos are adjusted to have the same contrast levels (100-1300). Yellow circles in the order from top to bottom correspond to the traces FIGS. 1.11a-f. The same excitation laser power (2.3 mW) and the same concentration of samples (20 pM) were used for both measurements.

FIG. 1.12 illustrates the fluorescence intensity distributions for FMNs labeled with A594 and Qdot 605. The total numbers of analyzed particles were 1251 and 515, respectively.

FIG. 2.1 illustrates FMN with surface RGD molecules specifically label human glioblastoma U87MG cancer cells. The blue color is for Dapi stained cells. The red color shows the fluorescence of FMN incorporated with Alexafluor 594. The combine column shows the overlay of the blue and red images.

FIG. 2.2 illustrates in vivo fluorescence detection sensitivity characterization of FMN-Cy5.5 using IVIS-spectrum. The excitation wavelength is 640 nm; the emission wavelength is selected at 700 nm. Samples were mixed with Matrigel® and injected subcutaneously.

FIGS. 2.3a-d illustrate MRI contrast development of an intramuscularly administered sample following multiple injections: FIG. 2.3a Pre-injection, FIG. 2.3b After first injection, FIG. 2.3c After second injection, and FIG. 2.3d After third injection. Each injection is with 2 pmol of sample. Clear contrast development (red curve outline) can be observed.

FIG. 2.4 illustrates a highly sensitive and correlated Fluorescence and MRI imaging with FMNs. 500 pM of FMNs can be clearly differentiated from the control sample without any contrast agents.

FIG. 2.5 illustrates intravital imaging shows that FMNs with surface RGD specifically bound to U87MG tumor neovasculature. The green color shows tumor cells which are transfected with GFP. The red color shows commercial vascular dye outlining tumor neovasculature. The white color is the fluorescence from FMNs.

FIGS. 2.6a-c illustrates FMNs responding to a magnetic microstructure. The features on the magnetic microstructure are 15 um×45 uM. FIG. 2.6a Bright field image; FIG. 2.6b Fluorescent image showing FMNs; FIG. 2.6c Overlay of FIG. 2.7a and FIG. 2.6b.

FIG. 2.7a illustrates FACS showing T-cells loaded with FMNs. Results from a few electroporation approaches are drawn in the same plot. FIG. 2.7b illustrates T-cells loaded with FMNs using X001 method respond to an external permanent magnet and condensed in proximity to one end of the magnet. The top panel shows the bright field image, and the bottom panel shows the fluorescent image indicating FMNs loaded inside T-cells.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of synthetic organic chemistry, biochemistry, biology, molecular biology, recombinant DNA techniques, pharmacology, imaging, and the like, which are within the skill of the art. Such techniques are explained fully in the literature.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

By "administration" is meant introducing a compound into a subject. The preferred route of administration of the compounds is intravenous. However, any route of administration, such as oral, topical, subcutaneous, peritoneal, intraarterial, inhalation, vaginal, rectal, nasal, introduction into the cerebrospinal fluid, or instillation into body compartments can be used.

As used herein, the term "host" or "organism" includes humans, mammals (e.g., cats, dogs, horses, etc.), living cells, and other living organisms. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a host.

The term "sample" can refer to a tissue sample, cell sample, a fluid sample, and the like. The sample may be taken from a host. The tissue sample can include hair (including roots), buccal swabs, blood, saliva, semen, muscle, or from any internal organs. The fluid may be, but is not limited to, urine, blood, ascites, pleural fluid, spinal fluid, and the like. The body tissue can include, but is not limited to, skin, muscle, endometrial, uterine, and cervical tissue. In the present disclosure, the source of the sample is not critical.

The term "detectable" refers to the ability to detect a signal over the background signal.

The term "detectable signal" is a signal derived from non-invasive imaging techniques such as, but not limited to, positron emission tomography (PET), single photon emission computed tomography (SPECT), or magnetic resonance imaging (MRI). The detectable signal is detectable and distinguishable from other background signals that may be generated from the host. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between detectable signal and the background. Standards and/or calibration curves can be used to determine the relative intensity of the detectable signal and/or the background.

The signal can be generated from one or more compounds of the present disclosure. In an embodiment, the signal may need to be the sum of each of the individual compounds. In an embodiment, the signal can be generated from a summation, an integration, or other mathematical process, formula, or algorithm, where the signal is from one or more compounds. In an embodiment, the summation, the integration, or other mathematical process, formula, or algorithm can be used to generate the signal so that the signal can be distinguished from background noise and the like.

The detectable signal is defined as an amount sufficient to yield an acceptable image using equipment that is available for pre-clinical use. A detectable signal may be generated by one or more administrations of the compounds of the present disclosure. The amount of the administered compound of the present disclosure can vary according to factors such as the degree of susceptibility of the individual, the age, sex, and weight of the individual, idiosyncratic responses of the individual, the dosimetry, and the like. The amount of the compounds of the present disclosure can also vary according to instrument and digital processing related factors.

"Cancer", "tumor", and "precancerous" as used herein, shall be given their ordinary meaning, as general terms for diseases in which abnormal cells divide without control. Cancer cells can invade nearby tissues and can spread through the bloodstream and lymphatic system to other parts of the body. In an embodiment, "cancer", "tumor", and "precancerous" refer to MMP-2 positive cancer, tumors, precancerous tissues, and the like. In an embodiment, the MMP-2 positive cancer, tumors, precancerous tissues, and the like, correspond to malignant tumors, including breast, lung, brain, colon, melanoma, gastric, and esophageal carcinomas.

There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it, with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors.

Representative cancers include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias such as, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as, but not limited to, chronic myelocytic (granulocytic) leukemia, chronic lymphocytic leukemia, hairy cell leukemia; polycythemia vera; lymphomas such as, but not limited to, Hodgkin's disease, non-Hodgkin's disease; multiple myelomas such as, but not limited to, smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as, but not limited to, bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as, but not limited to, pheochromocytoma and adrenocortical carcinoma; thyroid cancer such as, but not limited to, papillary or follicular thyroid cancer, medullary thyroid cancer and anaplastic thyroid cancer; pancreatic cancer such as, but not limited to, insulinoma, gastrinoma, glucagonoma, vipoma, somatostatin-secreting tumor, and carcinoid or islet cell tumor; pituitary cancers such as, but not limited to, Cushing's disease, prolactin-secreting tumor, acromegaly, and diabetes insipidus; eye cancers such as, but not limited to, ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as, but not limited to, squamous cell carcinoma, and adenocarcinoma; uterine cancers such as, but not limited to, endometrial carcinoma and uterine sarcoma; ovarian cancers such as, but not limited to, ovarian epithelial carcinoma, borderline tumor, germ cell tumor, and stromal tumor; esophageal cancers such as, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as, but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as, but not limited to, hepatocellular carcinoma and hepatoblastoma, gallbladder cancers such as adenocarcinoma; cholangiocarcinomas such as, but not limited to, papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as, but not limited to, germinal tumor, seminoma, anaplastic, classic (typical), spermatocytic, non-seminoma, embryonal carcinoma, teratoma carcinoma, choriocarcinoma (yolk-sac tumor), prostate cancers such as, but not limited to, adenocarcinoma, leiomyosarcoma, and rhabdomyosarcoma; penal cancers; oral cancers such as, but not limited to, squamous cell carcinoma; basal cancers; salivary gland cancers such as, but not limited to, adenocarcinoma, mucoepidermoid carcinoma, and adenoidcystic carcinoma; pharynx cancers such as, but not limited to, squamous cell cancer, and verrucous; skin cancers such as, but not limited to, basal cell carcinoma, squamous cell carcinoma and melanoma, superficial spreading melanoma, nodular melanoma, lentigo malignant melanoma, acral lentiginous melanoma; kidney cancers such as, but not limited to, renal cell cancer, adenocarcinoma, hypernephroma, fibrosarcoma, transitional cell cancer (renal pelvis and/or ureter); Wilms' tumor; bladder cancers such as, but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., inc., United States of America). It is also contemplated that cancers caused by aberrations in apoptosis can also be treated by the methods and compositions of the present disclosure. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes.

A tumor can be classified as malignant or benign. In both cases, there is an abnormal aggregation and proliferation of cells. In the case of a malignant tumor, these cells behave more aggressively, acquiring properties of increased invasiveness. Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult.

Benign tumors have less of a tendency to invade and are less likely to metastasize. Brain tumors spread extensively within the brain but do not usually metastasize outside the brain. Gliomas are very invasive inside the brain, even crossing hemispheres. They do divide in an uncontrolled manner, though. Depending on their location, they can be just as life threatening as malignant lesions. An example of this would be a benign tumor in the brain, which can grow and occupy space within the skull, leading to increased pressure on the brain.

It should be noted that cancerous cells, cancer, and tumors are sometimes used interchangeably in the disclosure.

General Discussion

Embodiments of the present disclosure include nanoprobes, methods of using nanoprobes, methods of making nanoprobes, and the like. Embodiments of the present disclosure provide for nanoprobes that have both magnetic and optical properties. In this regard, embodiments of the present disclosure can be imaged using both magnetic resonance imaging (MRI) techniques and fluorescent techniques, which is advantageous because MRI provides excellent spatial-resolution for molecular imaging and diagnostics, and optical imaging is very sensitive, less costly, and easy to implement. In particular, embodiments of the present disclosure have high saturation magnetization and MRI transverse relaxivity for MRI applications and excellent spectral tunability and brightness for fluorescence imaging. In addition, embodiments of the present disclosure demonstrate significant advantages for single molecule fluorescence imaging because of the superior single particle brightness and resistance to either blinking and/or fast photo-bleaching. Furthermore, embodiments of the present disclosure can include targeting moieties that can be used to image a target with embodiments of the nanoprobes. Moreover, embodiments of the present disclosure can be used together with an external magnetic field control, such as that from a magnetic stand of a permanent magnet, a microarray of magnetic materials, an electromagnet, or a combination thereof, to further improve the targeting and imaging capabilities of the nanoprobes.

In an embodiment, the nanoprobe can be a coated superparamagnetic iron oxide (SPIO) nanoparticle having a silanization coating on the surface of the SPIO nanoparticle. In addition, the nanoprobe includes one or more fluorescent compounds attached (e.g., directly or indirectly (e.g., using a cross-linker compound)) to the surface of coated SPIO nanoparticle.

In an embodiment, the surface (attached directly or indirectly) of the coated SPIO nanoparticle can include, but is not limited to, a targeting moiety, a drug, a therapeutic agent, a radiological agent, a chemological agent, a small molecule drug, a biological agent (e.g., peptides, proteins, antibodies, antigens, and the like) and combinations thereof, that can be used to image, detect, study, monitor, evaluate, and/or screen a disease, condition, or related biological event corresponding to the target. In an embodiment, the targeting moiety, the drug, the therapeutic agent, the radiological agent, the chemological agent, the small molecule drug, the biological agent, and combinations thereof, are attached (e.g., directly or indirectly) to the surface of the coated SPIO nanoparticle. In an embodiment, the nanoprobe can include multiple different components (e.g., targeting moieties, drugs, and the like) attached to the surface of the nanoprobe. In an embodiment, the targeting moiety, the drug, the therapeutic agent, the radiological agent, the chemological agent, the small molecule drug, and the biological agent, can each be attached to the coated SPIO nanoparticle using the same functional group or different functional groups on the surface of the coated SPIO nanoparticle.

In an embodiment, a targeting moiety can be attached (e.g., directly or indirectly) to the silanization coating, where the targeting moiety has an affinity (e.g., a preferential attraction towards as opposed to attraction towards non-targets) for a target (e.g., a cell, a tissue, a protein, an antibody, an antigen, and the like).

Embodiments of the coated SPIO nanoparticle can be used to provide high optical and/or magnetic contrast for imaging. In this regard, the coated SPIO nanoparticle can be used for imaging anatomical and/or physiological events in a host. Embodiments of the present disclosure enable the imaging of molecular events in vitro or in vivo using techniques and methods of the present disclosure. The image acquired using the techniques and methods of the present disclosure can be used to illustrate the concentration and/or location of the coated SPIO nanoparticle, which can be correlated to the target of interest or the like. It should be noted that embodiments of the present disclosure can provide fluorescence sensitivity that is improved 20 times when compared to quantum dot sensitivity.

Embodiments of the present disclosure can also be used in clinical settings where MRI could be used for pre-operative diagnostics and fluorescence imaging could be used to guide surgical intervention.

Embodiments of the present disclosure can be used in conjunction with intravital imaging. In this regard, intravital microscopy can be used to directly observe the interaction of the nanoprobes with living subjects.

The SPIO nanoparticle (magnetic signal inherent in the SPIO nanoparticle) can be measured and detected using an MRI system. The fluorescent energy can be detected and quantified in real time using an appropriate optical imaging detection system (e.g., a photomultiplier tube in a fluorometer and/or a luminometer, for example). In an embodiment, the detection system could be a combination of the optical imaging system and the MRI system.

The SPIO nanoparticle, without the silanization coating, is an iron oxide nanoparticle, either maghemite ($\gamma$-$Fe_2O_3$) or magnetite ($Fe_3O_4$), or nanoparticles composed of both phases. The SPIO can be synthesized through different methods, and dispersed as a colloidal solution in organic solvents or water. In an embodiment, the coated SPIO nanoparticle is superior to the uncoated SPIO nanoparticles, as described in more detail herein and in the Examples.

SPIO nanoparticles can be made using one or more methods. In an embodiment, the SPIO nanoparticle is a product of an oxidative decomposition of iron pentacarbonyl with trimethylamine oxide, oleic acid, and hexadecane. In an embodiment, the SPIO nanoparticle is a product of co-precipitation of ferrous and ferric salts in an alkaline medium.

In an embodiment, the SPIO nanoparticle can be generally spherical, semi-spherical, oval, or a similar three dimensional shape.

In an embodiment, the SPIO nanoparticle can have a diameter (or the longest dimension of the SPIO nanoparticle) of about 2 to 40 nm (i.e., the superparamagnetic size limit for iron oxide nanoparticles). In another embodiment, the SPIO nanoparticle can have a diameter of about 5 to 10 nm. In another embodiment, the SPIO nanoparticle can have a diameter of about 5 nm. In another embodiment, the SPIO nanoparticle can have a diameter of about 7 nm. In another embodiment, the SPIO nanoparticle can have a diameter of about 9 nm. In another embodiment, the SPIO nanoparticle can have a diameter of about 15 nm. In an embodiment, if the nanoparticle is not spherical or semi-spherical, then the longest dimension of the nanoparticle is equivalent to the diameter and can have any one of the diameters (longest dimension) noted above.

The coated SPIO nanoparticle is coated with a silanization coating. In an embodiment, the silanization coating is a coating including silane and/or silane-like molecules (or the reaction products of those molecules with the surface) onto the surface of the SPIO nanoparticles. The coating can be amorphous. The thickness of the coating can be controlled so that coated SPIO nanoparticles can be created for particular applications. In an embodiment, the silanization coating is made by cross-linking of trimethoxyl silanes with appropriate functional groups, such as a mercapto group, an amino group, a mercapto/amino group, a carboxyl group, a phosphonate group, an alkyl group, a polyethylene oxide group (PEG), and combinations thereof.

In an embodiment, the silanization coating can be about 1 to 5 nm thick. In an embodiment, the silanization coating can be about 1 to 10 nm thick. In an embodiment, the silanization coating can be about 1 to 20 nm thick. In an embodiment, the silanization coating can be about 1 to 30 nm thick. In an embodiment, the silanization coating can be about 1 to 40 nm thick. In an embodiment, the silanization coating can be about 1 to 50 nm thick. In an embodiment, the silanization coating can be about 1 to 60 nm thick. In an embodiment, the silanization coating can be about 1 to 100 nm thick. In an embodiment, the silanization coating can be about 1 to 500 nm thick. In an embodiment, the silanization coating can be about 1 to 1000 nm thick. In an embodiment, a silanization thickness of 2-3 nm is enough to provide a robust coating that will keep SPIO stable (e.g., no aggregates or sediments formed) inside physiological buffer (e.g., phosphate buffered saline with a pH of about 7.3) for greater than 6 months, greater than a year, 3-5 years, or longer. Thicker silanization coating can also be rationally controlled by adding a larger amount of trimethoxyl silane reagents or using sodium silicate.

In an embodiment, the coated SPIO nanoparticle can have a diameter (or the longest dimension of the coated SPIO nanoparticle) of about 1 to 1000 nm. In another embodiment, the coated SPIO nanoparticle can have a diameter of about 1 to 100 nm. In another embodiment, the coated the SPIO nanoparticle can have a diameter of about 1 to 30 nm. In another embodiment, the coated the SPIO nanoparticle can have a diameter of about 500 nm. In another embodiment, the coated SPIO nanoparticle can have a diameter of about 100 nm. In another embodiment, the coated SPIO nanoparticle can have a diameter of about 50 nm. In another embodiment, the coated SPIO nanoparticle can have a diameter of about 30 nm. In another embodiment, the coated SPIO nanoparticle can have a diameter of about 10 nm.

The coated SPIO nanoparticle having the silanization coating can have one or more of the following characteristics. The coated SPIO nanoparticles have the same saturation magnetization as the original SPIO, indicating that the silanization coating does not change or significantly change (e.g., less than 10%, less than 5%, less than 4%, less than 3%, less than 2%, or less than 1%) the magnetic properties of the original SPIO. The coated SPIO nanoparticles are very stable in physiological solutions (e.g., phosphate buffered saline with a pH of about 7.3) and do not aggregate over long periods of time (e.g., 1 year or more).

In an embodiment, the coated SPIO nanoparticle can have one or more fluorescent compounds (e.g., the same type or different types) attached (e.g., directly or indirectly) to the silanization coating. In particular, the coated SPIO nanoparticle can include about 1 to 500 fluorescent compounds attached to the silanization coating. In an embodiment, two or more types of fluorescent compounds can be attached to the silanization coating. The types of fluorescent compounds can be attached using the same type or different types of functional groups on the surface of the coated SPIO nanoparticles.

Embodiments of the fluorescent compounds (fluorophores) can include, but are not limited to: 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AFPs—AutoFluorescent Protein—(Quantum Biotechnologies); Alexa® Fluor 350; Alexa® Fluor 405; Alexa® Fluor 500; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; Bimane; Bisbenzamide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson™, Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; Chlorophyll; Chromomycin A; Chromomycin A; CL-NERF; CMFDA; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3' DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD—Lipophilic Tracer; DiD (DiIC18(5)); DIDS; Dihydrorhodamine 123 (DHR); DiI (DiIC18(3)); Dinitrophenol; DiO (DiOC18 (3)); DiR; DiR (DiIC18(7)); DM-NERF (high pH); DNP; Dopamine; DTAF; DY-630-NHS; DY-635-NHS; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf; JC-1; JO-JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin EBG; Oregon Green; Oregon Green 488-X; Oregon Green™, Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine BB; Rhodamine B extra; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); S65A; S65C; S65L; S65T; SBFI; Serotonin; Sevron Brilliant Red 2B; Sevron Brilliant Red 4G; Sevron Brilliant Red B; Sevron Orange; Sevron Yellow L; SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO- 3; TriColor (PE-Cy5); TRITC TetramethylRodamineIsoThioCyanate; True Blue; TruRed; Ultralite; Uranine B; Uvitex SFC; WW 781; X-Rhodamine; XRITC; Xylene Orange; Y66F; Y66H; Y66W; YO-PRO-1; YO-PRO-3; YOYO-1; YOYO-3, Sybr Green, Thiazole orange (interchelating dyes), or combinations thereof.

In an embodiment, the fluorescent compounds (fluorophores) can include, but are not limited to: fluorescein; Alexa Fluor 488™; Alexa Fluor 594™; Alexa Fluor 680™; and Cy5.5™ with appropriate functional groups, such as those noted herein, or their streptavidin conjugates.

In an embodiment, the fluorescent compounds or the other agents noted above can be attached directly and/or indirectly (e.g., using one or more linker compounds) to the silanization coating. In an embodiment, the fluorescent compounds can be attached directly or indirectly to the silanization coating via chemical bonding (e.g., covalently or ionically), biological interaction, biochemical interaction, and/or otherwise associated with one another. In particular, the fluorescent compounds can be attached directly or indirectly to the silanization coating via a covalent bond, a non-covalent bond, and/or an ionic bond, as well as being attached through interactions such as, but not limited to, chelation interactions, hydrophobic interactions, hydrophilic interactions, charge-charge interactions, π-stacking interactions, combinations thereof, and like interactions.

In an embodiment, the fluorescent compounds or the other agents noted above can be attached to the silanization coating using one or more functional groups on the surface or extending from the surface of the silanization coating. In an embodiment, the functional groups can be incorporated into the silanization coating using the components to prepare the silanization coating, where one or more of the components include functional groups that are assessable to the fluorescent compounds so that they can interact and attach to the fluorescent compounds. In an embodiment, the functional groups can be incorporated into the silanization coating after the silanization coating is formed on the SPIO nanoparticle.

In an embodiment, the functional groups can include, but are not limited to, amino groups, mercapto groups, carboxyl groups, phosphonate groups, alkyl groups, polyethylene oxides, and combinations thereof. In an embodiment, the number of functional groups (the same type or different types) attached to the silanization coating can range from about 1 to 500. In an embodiment, two or more functional groups can be selected to be incorporated into the coating of the coated SPIO nanoparticle so that different types of agents (e.g., targeting moieties, fluorescent groups, drugs, and the like) can be attached to the coated SPIO nanoparticle.

In an embodiment, the fluorescent compounds can be attached to the silanization coating using techniques involving biotin-avidin (streptavidin) interactions (e.g., biotin-streptavidin (e.g., the streptavidin is labeled with a fluorescent compound)), antibody-antigen interactions, apatameter-protein interactions, DNA-complementary DNA hybridization, and combinations thereof. Biotin with appropriate functional groups (e.g., maleimide functionalized Biotin) can covalently bind to the surface functional groups of the silanization coating (e.g., mercapto groups).

As mentioned above, the coated SPIO nanoparticle includes a targeting moiety. In an embodiment, the targeting moiety can target (e.g., have an affinity for) disease, disease related conditions, and related biological events that correspond to the disease. In an embodiment, the targeting moiety can target precancerous tissue, cancer, tumors, and related biological events (e.g., proteins present when certain cancers are present), as well as other diseases or conditions.

In an embodiment, a targeting moiety can be attached (e.g., directly or indirectly) to the silanization coating. The targeting moiety has an affinity for a target (e.g., a cell, a tissue, a protein, an antibody, an antigen, and the like). The targeting moiety can include, but is not limited to, polypeptides (e.g., proteins such as, but not limited to, antibodies (monoclonal or polyclonal)), antigens, nucleic acids (both monomeric and oligomeric), polysaccharides, sugars, fatty acids, steroids, purines, pyrimidines, ligands, or combinations thereof. In an embodiment, the targeting moiety has an affinity for one or more targets. In general, the target can include, but is not limited to, a cell type, a cell surface, extracellular space, intracellular space, a tissue type, a tissue surface, vascular, a polypeptide, a nucleic acid, a polysaccharide, a sugar, a fatty acid, a steroid, a purine, a pyrimidine, a hapten, a ligand, and the like, related to a condition, disease, or related biological event or other chemical, biochemical, and/or biological event of the sample or host. The targeting moiety can be selected based on the target selected and the environment the target is in and/or conditions that the target is subject to.

In an embodiment, the targeting moiety can be selected to have an affinity (e.g., an attraction to) for a target such as, but not limited to, a specific protein, a cell type, a receptor, a transporter, an antigen, and a saccharide (e.g., a monosaccharide, a disaccharide and a polysaccharide), as well as other molecules that can interact with the targeting moiety. The targeting moiety can include, but is not limited to, an antibody, an antigen, a polypeptide, an aptamer, a small molecule, and ligands, as well as other molecules that bind to the target.

In an embodiment, the targeting moiety can include a RGD containing peptide (corresponding to integrin $\alpha_v\beta_3$ target) (e.g., a peptide that includes RGD but may include one or more (e.g., 2) amino acids). In an embodiment, molecules that can be targets include, but are not limited to, integrin $\alpha_v\beta_3$, vascular receptors (e.g., Vascular endothelial growth factor receptor (VEGF-R)), extracellular matrix proteins (e.g., proteases, MMP, thrombin), cell membrane receptors (e.g., epidermal growth factor receptor (EGFR) (e.g., HER2)), intracellular proteins, enzymes (e.g., caspases and PSA), serum proteins (e.g., albumin), and the like.

The targeting moiety can be linked, directly or indirectly, in a manner described herein using a stable physical, biological, biochemical, and/or chemical association. In an embodiment, the targeting moiety can be independently linked to the silanization coating using, but not limited to, a covalent link, a non-covalent link, an ionic link, a chelated link, as well as being linked through interactions such as, but not limited to, hydrophobic interactions, hydrophilic interactions, charge-charge interactions, π-stacking interactions, combinations thereof, and like interactions. In an embodiment, the targeting moiety can be attached using a linker or cross-linker compound.

In an embodiment, the coated SPIO nanoparticles of the present disclosure can also include drug molecules that can provide therapeutic treatment to the target of interest. Embodiments of the present disclosure can also be associated with metal chelators (e.g., 1,4,7,10-tetraazadodecane-N,N,N, N-tetraacetic acid (DOTA)) and labeled with a positron-emitting isotope (e.g., $^{64}Cu$) for additional imaging contrast capability, such as PET imaging.

In an embodiment, the silanization of the SPIO nanoparticles from coated SPIO nanoparticles can have amino groups and mercapto groups on the surface of the coated SPIO nanoparticles. N-hydroxysuccinimide (NHS) ether functionalized fluorophores can be covalently attached to the surface of the coated SPIO nanoparticle via the amino groups. In addition, targeting moieties can be covalently attached to the surface of the coated SPIO nanoparticle via the mercapto groups. In an embodiment, the targeting moiety has an amino functional group that can attach to the surface of the coated SPIO nanoparticle using a cross-linker such as sulfosuccinimidyl-4-[N-maleimidomethyl]cyclohexane-1-carboxylate (sulfo-SMCC), for example. Other possible cross-linkers include 1-ethyl-3-[3-dimethylaminopropyl]carbodiimide hydrochloride (EDAC) and its derivatives, and sulfo-SMCC derivatives.

By binding the fluorophores and the targeting moieties using different functional groups on the surface of the coated SPIO nanoparticle, the amount of each of the fluorophores and the targeting moieties can be independently controlled. In an embodiment, three or more functional groups can be on the surface of the coated SPIO nanoparticle so that three or more fluorophores, targeting moieties, drugs, and the like can be attached to the surface of the coated SPIO nanoparticle.

Methods of Use

As mentioned above, the present disclosure relates generally to methods for studying (e.g., detecting, localizing, and/or quantifying) cellular events, molecular events, in vivo cell trafficking, stem cell studies, vascular imaging, tumor imaging, biomolecule array systems, biosensing, biolabeling, gene expression studies, protein studies, medical diagnostics, diagnostic libraries, microfluidic systems, and delivery vehicles. The present disclosure also relates to methods for multiplex imaging of multiple events substantially simultaneously inside a subject (e.g., a host living cell, tissue, or organ, or a host living organism) using two or more coated SPIO nanoparticles.

In short, the coated SPIO nanoparticles are introduced to the system (sample or host) using known techniques (e.g., injection, oral administration, and the like) to determine if the system includes one or more targets. At an appropriate time, the sample (e.g., living cell, tissue, or organ) or host is illuminated with an optical energy. In addition, the sample or host is exposed to an MRI system to detect the SPIO nanoparticles. The detection system could be a combination of the optical imaging system and the MRI system of the systems can be independent of one another. In an embodiment, the appropriate time may include a time frame to allow unassociated coated SPIO nanoparticles to be sufficiently cleared from the appropriate area, region, or, tissue of interest. The fluorescence signal and the magnetic signal can be detected and measured using systems described herein or known systems. In an embodiment, the detection and measurement of the optical energy and the magnetic energy can be used to determine the presence and/or location of the target of interest. In an embodiment, the method may include detecting the MRI image in a clinical setting where MRI could be used for pre-operative diagnostics and the fluorescent imaging could be used to guide surgical intervention.

The fluorescent signal and/or the magnetic signal can be measured, detected, and quantified in real time using a detection system. The measured signals are or can be correlated to the feature being studied.

In an embodiment, the coated SPIO nanoparticles can be used to study, image, diagnose the presence of, and/or treat cancerous cells, precancerous cells, cancer, or tumors. For example, the presence of the cancerous cells, precancerous cells, cancer, or tumors can provide insight into the appropriate diagnosis and/or treatment. It should be noted that coated SPIO nanoparticles could include an agent specific for other diseases or conditions so that other diseases or conditions can be imaged, diagnosed, and/or treated using embodiments of the present disclosure. In an embodiment, other diseases and/or conditions can be studied, imaged, diagnosed, and/or treated in a manner consistent with the discussion below as it relates to cancerous cells, precancerous cells, cancer, and/or tumors.

In another embodiment, the coated SPIO nanoparticles include one or more agents to treat the cancerous cells, precancerous cells, cancer, or tumors. Upon measuring or detecting the fluorescent signal and the magnetic signal, one can determine if the coated SPIO nanoparticles have coordinated with the cancerous cells, precancerous cells, cancer, or tumors. Embodiments of the coated SPIO nanoparticles can aid in visualizing the response of the cancerous cells, precancerous cells, cancer, or tumors to the agent.

In general, the coated SPIO nanoparticles can be used in a screening tool to select agents for imaging, diagnosing, and/or treating a disease or condition. In an embodiment, the coated SPIO nanoparticles can be used in a screening tool to select agents for imaging, diagnosing, and/or treating cancerous cells, precancerous cells, cancer, or tumors. The coated SPIO nanoparticles can be imaged and it can be determined if each agent can be used to image, diagnose, and/or treat cancerous cells, precancerous cells, cancer, or tumors.

It should be noted that the amount effective to result in uptake of the compound into the cells or tissue of interest will depend upon a variety of factors, including for example, the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts.

Kits

This disclosure encompasses kits that include, but are not limited to, coated SPIO nanoparticles and directions (instructions (written or digital (e.g., CD or DVD)) for their use). The components listed above can be tailored to the particular event being studied, imaged, and/or treated (e.g., cancer, cancerous, or precancerous cells). The kit can further include appropriate buffers and reagents known in the art for administering various combinations of the components listed above to the host cell or host organism.

EXAMPLES

Now having described the embodiments of nanoprobes, systems, and methods of use, in general, the examples describe some additional embodiments of the present disclosure. While embodiments of present disclosure are described in connection with the examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

In this example, we describe a versatile approach to synthesize multifunctional nanoprobes with superior magnetic and optical properties. These nanoprobes have high saturation magnetization and MRI transverse relaxivity, essential for advanced MRI applications. At the same time, they exhibit excellent spectral tunability and brightness for fluorescence imaging. When further decorated with targeting molecules, they are able to label and track specific cell surface proteins over long periods of time at the single molecule level. These nanoprobes are highly promising for many biomedical imaging applications where superior magnetic and optical properties are needed.

Particle size and shape, material component, surface chemistry and functional properties are all very important for their biomedical applications. The preparation approach of the nanomaterials that determines these material traits represents one of the largest challenges for any desired diagnostic and therapeutic purpose. Being non-toxic and non-immunogenic, iron-oxide based nanoparticles (magnetite $Fe_3O_4$ and maghemite $\gamma$-$Fe_2O_3$) are the most commonly used magnetic nanoparticles for biomedical applications.[13] Feridex®, made from superparamagnetic iron oxide (SPIO) nanoparticles, is FDA approved and has been used as a clinical MRI contrast agent for over a decade.[14,15] Here, we sought to begin from a single SPIO with well defined size and magnetization to develop multifunctional magnetic and fluorescent nanoprobes.

SPIO nanoparticles were synthesized by oxidative decomposition of iron pentacarbonyl with trimethylamine oxide, oleic acid and hexadecane based on previously reported methods.[16] Size and structural characterizations of these nanoparticles are shown in FIG. 1.6. Then, a thin layer surface silanization coating method[17,18] was adapted to transfer SPIO nanoparticles from organic solution into a water soluble and bio-compatible form. SPIO nanoparticles after silanization (siSPIO or coated SPIO) were very stable within physiological buffer solutions. No aggregation or sedimentation was observed over long periods of time (>1 year). Shown in the inset of FIG. 1.1a, a siSPIO sample aged for over 1 year is still clearly suspended inside phosphate buffered saline (PBS), while as-synthesized SPIO nanoparticles only dissolve in organic solvents.

The magnetic properties of siSPIO and SPIO were characterized by alternating gradient magnetometry (AGM), which allows measurements of the magnetization of very small amounts (<10 μl) of magnetic particle solutions. FIG. 1.1a shows the magnetization curves from the AGM measurements. The absence of hysteresis, remanence and coercivity is characteristic of the superparamagnetic nature of the nanoparticles. The magnetic responses of the SPIO nanoparticles change negligibly after silanization coating. Both siSPIO and SPIO have a saturation magnetic field strength of roughly 5 k Oe, and the same saturation magnetization (Ms, normalized to Fe mass throughout this paper) of 105 emu·$g^{-1}$ Fe, indicating that the silanization process is highly applicable for the surface modification of SPIO nanoparticles. As a silanization coating with a thickness as small as 2-3 nm is sufficient to provide stable aqueous suspension of various nanoparticles,[17,18] its robustness and versatility is desirable for various biomedical applications.

The ability of siSPIO to shorten proton transverse (T2) relaxation time for MRI was measured and compared with the commercial MRI contrast agent Feridex® in a 1.5 T magnetic field. The measured transverse relaxation rates are plotted as a function of Fe concentration in FIG. 1.1b, and a representative $T_2$-weighted MR image is shown in FIG. 1.1c. From transverse relaxivity ($r_2$) values derived from the slopes of the linear fit of the relaxation rates vs. Fe concentration data, we found that the $r_2$ relaxivity of siSPIO (156 $mM^{-1}S^{-1}$) was much higher than that of commercial Feridex® (102 $mM^{-1}S^{-1}$). The higher relaxivity, hence the better MRI contrast, could be attributed to the higher Ms of siSPIO. To better illustrate the effect of saturation magnetization Ms on MRI $r_2$ relaxivity, we also included in our measurement the MRI relaxivity of a control siSPIO that was silanized from a non-optimized organic SPIO sample. The control siSPIO had the smallest Ms of 43 emu·$g^{-1}$ Fe hence the lowest $r_2$ relaxivity of 45 $mM^{-1}S^{-1}$, Feridex® had an intermediate Ms of 70 emu·$g^{-1}$ Fe and an intermediate $r_2$ relaxivity of 102 $mM^{-1}S^{-1}$, and the siSPIO had the largest Ms of 105 emu·$g^{-1}$ Fe and the highest $r_2$ relaxivity of 156 $mM^{-1}S^{-1}$. Such monotonic dependence of MRI relaxivity on Ms is reasonable because proton transverse (spin-spin) relaxations facilitated by surrounding magnetic nanoparticles lead to shortened $T_2$ time.[1,5,19] Careful control of the synthetic and coating process allows us to engineer the magnetism of SPIO and hence its capability in providing enhanced MRI contrast. The high Ms and MR transverse relaxivity observed for our siSPIO are comparable to the high performance superparamagnetic nanoparticles recently developed for ultra-sensitive magnetic resonance molecular imaging.[1] Various MRI applications such as tumor vasculature imaging[20], early cancer detection,[1] and lymphotrophic contrast agents[15] can be easily envisioned for siSPIO alone; however, developing siSPIO into fluorescent magnetic nanoprobes will provide the added benefit of combining the superior spatial resolution and volumetric tomographic capability of MRI with the high sensitivity, convenience and economy of fluorescence optical imaging.[8]

We utilized the richness of silane chemistry to further develop siSPIO into fluorescent magnetic nanoprobes (FMNs). Because many functional groups, such as amino, mercapto, and carboxyl can be easily incorporated into the silane coating, common bioconjugation techniques can be used to attach various organic fluorophores onto the siSPIO surface. Two general incorporation procedures are illustrated in the cartoon of FIG. 1.2a. Starting from siSPIO with surface mercapto groups, organic fluorophores with maleimide modification could be directly conjugated to the siSPIO surface by covalent bonding. Alternatively, other molecular linkages such as biotin-streptavidin interactions could also be used for fluorophore incorporation. In the gel-electrophoresis image of FIG. 1.2b, FMN of siSPIO conjugated with Alexa Fluor® 594 (A594) runs as a discrete band (right lane), with mobility that is clearly retarded from that of free A594 (left lane). FMNs were also made from siSPIO incorporated with streptavidin-fluorophores and examined using the gel-electrophoresis technique. (FIG. 1.7) The incorporation of fluorophores did not interfere with the magnetic properties of the siSPIO, as the magnetization measurement showed the same magnetic response for the FMN samples. (FIG. 1.2c) Our methodology is quite general and has consistently yielded FMNs with excellent fluorescence tunability across a wide range of wavelengths. (FIG. 1.8 and FIGS. 1.8a and 1.8b)

Our FMNs exhibited very high fluorescent intensity. One of the factors that contribute to this is the high valency on the siSPIO surface. Because of the large surface area of the nanoparticle and the relatively small space that each silane functional group occupies, a large number of fluorophores could be conjugated to the siSPIO surface to achieve very high fluorescence. More interestingly, a fluorescence stabilization effect was observed in our experiments. In solution, free organic fluorophores showed various degrees of fluorescence instability (FIG. 1.9), which could arise from chemical quenching caused by molecular oxygen or other ions in solution.[21,22] However, after binding to the siSPIO surface, organic fluorophores showed highly stable fluorescence signals in solution. An example of the fluorescence stabilization effect of FMNs as a function of the concentration of A594 is provided in FIG. 1.10.

The fluorescence stabilization was a general effect observed for all of the FMNs we synthesized. We have used different fluorophores including fluorescein, Alexa Fluor® dyes with various emission wavelengths, and Cy5.5®. These fluorophores were with different functional groups or in the form of streptavidin-conjugates. As shown in FIGS. 1.3a and 1.3b, after overnight incubation in PBS, fluorophores incorporated in FMNs are much brighter than unincorporated fluorophores. The fluorescence emission peak intensity of FMNs incorporated with Alexa Fluor® 488 (A488), A594, Alexa Fluor® 680 (A680), Cy5.5, streptavidin-A488 (A488s), streptavidin-Fluorescein (Fs), streptavidin-A594 (A594s) and streptavidin-A680 (A680s) are 1.1, 9.2, 2.5, 2.6, 18.8, 25.0, 109.3, and 5.5 times that of unincorporated fluorophores, respectively. These brightness differences between corresponding FMNs and unincorporated fluorophores are clearly correlated to the solution instability of fluorophores measured at the same fluorophore concentration (300 nM, FIG. 1.9). Further, slight red-shifts of the emission-profiles of incorporated fluorophore were also observed for most FMN samples. Previously, people reported the synthesis of fluorescent silica particles and suggested protection of the encapsulated fluorophores upon the addition of a siliceous shell.[23] The fluorescent stabilization effect observed in our experiments from a siliceous surface is likely a related phenomenon, however, the surface effect is more amenable to biological imaging applications, as it allows much easier tuning of the particle fluorescence wavelength and brightness level. Although the exact origin of this effect still warrants further investigation, the strong fluorescence achievable for fluorophores in proximity to the biocompatible and versatile siliceous structures can be very useful.

We characterized FMNs using fluorescence correlation spectroscopy (FCS). In FCS, the fluorescence signal from freely diffusing molecules in a solution is recorded as they pass through the focal volume of a fluorescence microscope. By analyzing the autocorrelation function of the fluctuations in the fluorescence intensity, various properties of the fluorescent molecules such as the concentration, the diffusion coefficient, the hydrodynamic diameter and the single particle brightness can be obtained.[24,25] Experimental details for the FCS measurement are described in the Supplementary information mentioned below. FIG. 1.3c shows the FCS correlation curves of two FMN samples with different numbers of A594 on the siSPIO surface, together with the correlation curves of free A594 (peak emission of 611 nm) and quantum dots (Qdots, streptavidin coated with peak emission of 607 nm, Invitrogen). All correlation curves are fitted well with the single species 3D diffusion model, indicating that all samples were monodispersed. Average single particle brightness calculated by dividing average fluorescence intensity by the number of molecules from FCS is displayed in FIG. 1.3d. By incorporating very bright Alexa Fluor® dyes, FMNs were easily controlled to have fluorescence brightness at the same level or even higher than that of the Qdots. The superior fluorescence characteristics of FMNs are also directly evident in the single particle fluorescence images (FIGS. 1.3e and 1.3f). Although the fluorescence intensity of single FMN particles decreased upon continuous laser excitation from photobleaching of incorporated organic fluorophores, they were bright enough to allow single FMN imaging for a long period of time (>30 s). When excited at the same laser power, single organic fluorophores could only fluoresce for a few seconds before complete photobleaching (data not shown). In addition, FMNs did not show any blinking (FIG. 1.3e) in contrast to Qdots (FIG. 1.3f). Blinking, the intermittency of the fluorescence signal, is an undesirable and random process exhibited by many fluorophores, including semiconductor quantum dots[26], organic dye molecules[27], and engineered fluorescent proteins[27]. Although Trolox or β-mercaptoethanol in combination with some oxygen scavenging system could potentially suppress blinking of organic fluorophores in single molecule fluorescence experiments,[28] additives like these are incompatible with many live biological systems. The strong fluorescence and non-blinking feature of FMNs are therefore advantageous when they are used for probing dynamic properties of biological molecules, such as in enzymatic processes and neuronal signaling, where uninterrupted imaging for seconds or even minutes is critical.[29,30]

We explored using FMNs for biological fluorescence imaging applications by specifically labeling and tracking synaptotagmin, a key molecule in regulating neurotransmitter release, in live neurons.[31] To render FMNs specific binding capability towards synaptotagmin, we first covalently linked streptavidin to the FMN surface. The surface streptavidin could then bind to the biotinylated synaptotagmin antibody. This method utilizes the strong and specific association between streptavidin and biotin, and can be easily extended to other ligand receptor binding schemes. In FIG. 1.4a, the green channel fluorescence images show the presynaptic boutons of a nerve terminal. These punctate like structures are specifically labeled by expression of a specific presynaptic marker synaptophysin fused with green fluorescent protein (GFP). Through binding with biotinylated synaptotagmin antibody, Streptavidin-FMNs (with A594, emission peak 611 nm) and streptavidin-Qdots (emission peak 607 nm) specifically labeled the surface exposed synaptotagmin in the plasma membrane of the presynaptic nerve terminal. (FIG. 1.4a, red channel) Although this imaging set-up was optimized for visualizing Qdots, the fluorescence signals of FMNs were clearly resolvable and comparable to that of Qdots. Further, a single FMN-labeled synaptotagmin could be continuously tracked over a long period of time (>80 s), while a single Qdot-labeled synaptotagmin unpredictably went into dark states caused by blinking. (FIG. 1.4b) This demonstrated that FMNs are advantageous for single molecule live cell imaging experiments compared to existing materials.

We further illustrated the capability of FMNs for correlated MRI and optical imaging. FMNs made with siSPIO and A680s were electrophoresed inside an agarose gel in comparison with free A680s at the same concentration. The gel phantom was then scanned with a small animal fluorescence imaging instrument IVIS® 200 (Xenogen). Strong near infrared (NIR) fluorescence signal was collected from the FMN sample. For the control samples of free A680s, the fluorescence intensities were much weaker. The strong fluorescence of FMNs and their capability in protecting incorporated fluorophores in a tissue mimicking situation is clearly illustrated in FIG. 1.5. At the same time, only the FMN sample exhibited strong contrast enhancement for both T2 and T2* weighted MR images measured in a 1.5T human whole body MRI scanner. This demonstrated that FMN is a high performance contrast agent capable of superior and multimodal NIR and MR imaging.

In addition to the high Ms and MR transverse relaxivity, superior fluorescence tunability and brightness, and resistance to single molecule fluorescence blinking, FMNs have a small hydrodynamic radius (7.5 nm for the smallest FMN measured); they are made with very biocompatible composite materials; and they are amenable to further derivation with targeting and therapeutic molecules. We expect FMNs and the general methodology that we developed in integrating different functional properties into a single nanoparticle will be very useful for various biomedical applications that require high performance multifunctional materials.

Methods

Preparation of FMNs

SPIO was synthesized following the published procedure[16] and stored at room temperature. The silanization coating procedure was adapted from previous work[17,18]. 600 µl of organic SPIO was precipitated out using isopropanol, and then 300 µl of mercapto-propyl trimethoxyl silane (mps) and 1000 µl TMAOH were added and sonicated for 2 h. Afterwards, the solution was diluted by adding 6 ml of a solution of 800 ml methanol and 2000 µl TMAOH, and then dialyzed in the same solution for 1 h. Then, 36 µl millipore water, 4 µl mps or amino-propyl trimethoxyl silane (aps) and 800 µl PEG-silane was added and sonicated for 1.5 h. The solution was then mixed with 0.1 ml chlorotrimethoxyl silane, 1.5 ml methanol and 0.32 g of solid TMAOH and sonicated for 2 h. Afterwards, the sample was condensed using Microcon YM-100 filters. The concentrated sample was dialyzed in 1 L of 10 mM PB (pH 7.3) overnight. The resulting water-soluable siSPIO was kept at 4° C. For fluorophore incorporation to form FMNs, maleimide or tetrafluorophenyl (TFP) ester modified fluorophores (Invitrogen or GE Healthcare) are reacted with mercapto-siSPIO or amino-siSPIO, respectively. The reaction time is ranged from 2 to 4 h to make FMN samples that will go through subsequent purification steps, or overnight to make FMN samples for fluorescence comparison experiments with free fluorophores. To purify the FMNs samples, a NAP-5 column (GE Healthcare) was used first, and then the collected solution was condensed and washed with Microcon YM-100 filters. For streptavidin-conjugated fluorophores, EZ-Link™ Biotin—BMCC (Pierce) was firstly reacted with mercapto-siSPIO for 2 h to provide surface biotins through thio-ether linkage. The sample was then purified using a NAP-5 column and Microcon YM-100 filters. Resultant biotin-siSPIO was incubated with streptavidin-fluorophores (Invitrogen) overnight to form FMNs. FMNs with streptavidin-fluorophores could also be purified with Microcon YM-100 filters.

Characterization

Fe concentration of all samples described in this paper was quantified using inductively coupled plasma—optical emission spectroscopy (TJA IRIS Advantage/1000 Radial ICAP Spectrometer). Magnetic properties were measured using a MircroMag 2900 alternating gradient magnetometer (AGM). The magnetic field range is −15 kOe to 15 kOe with 10 Oe step size. Ensemble solution fluorescence was obtained using a FluoroMax-3 spectrofluorometer (Jobin Yvon horiba). Ensemble solution fluorescence intensity was also measured by a TECAN SAFIRE microplate reader (Tecan Group). Optical absorbance was measured on an HP-8453 UV-Vis spectrophotometer (Hewlett-Packard). The concentration of each fluorophores (except otherwise specified) were determined by the Beer's law using the UV-Vis absorbance (the cell path length=1 cm) and the following extinction coefficients. Alexa fluoro-594: $\epsilon(590\ nm)=73,000\ M^{-1}\ cm^{-1}$; Alexa Fluoro-488: $\epsilon(490\ nm)=71,000\ M^{-1}\ cm^{-1}$; Cy5.5: $\epsilon(675\ nm)=250,000\ M^{-1}\ cm^{-1}$; Alexa fluoro-680: $\epsilon(680\ nm)=184,000\ M^{-1}\ cm^{-1}$; FITC: $4495\ nm)=73,000\ M^{-1}\ cm^{-1}$.

Magnetic Resonance Imaging (MRI) Measurements

MRI measurements of the transverse relaxation rates were performed using a 1.5 T whole-body scanner (Signa, GE Healthcare) and a 5-inch surface coil. The field of view was 12 cm by 12 cm. The slice thickness was 4 mm. The imaging matrix size was 256 by 128. T2 measurements were made using a spin-echo sequence with TR of 2,000 ms and TE of 10-160 ms. The resulting signal amplitudes were fit to mono-exponential decays through non-linear least-square fits (MATLAB, Mathworks, Cambridge, Mass.), and the fitted relaxation rates were taken as $R_2$ (spin-echo measurements). T2*-weighted MR image was obtained using a gradient-echo sequence with a 10° flip angle, 100 ms repetition time (TR) and echo time (TE) of 40 ms.

Gel-Electrophoresis Experiments

For gel-shift assay used to examine the incorporation of fluorophores with siSPIO, 3% agarose gel was used. Gel-electrophoresis was performed in 0.5× tris-Borate-EDTA buffer at 10 V/cm for 30 min. The gel images were acquired using BioDoc-It™ Imaging System (UVP, LLC). For the gel experiment used to illustrate correlated NIR-MRI imaging of FMN, 1% agarose gel was used, and it was run in 0.5× tris-Borate-EDTA buffer at 10 V/cm for 20 min. The gel was imaged in an IVIS® 200 imaging system (Xenogen) with Cy5.5 filters, acquisition time 1 s.

Fluorescence Correlation Spectroscopy (FCS) Measurements

All FCS experiments were performed on an inverted microscope (TE300, Nikon, USA), which was modified for confocal fluorescence detection. A 532 nm laser beam (Compass 215M, Coherent, USA), guided by an optical fiber and collimated with a 5× objective lens, was sent to the microscope as an excitation source. The laser beam was focused by a high numerical aperture objective (60×, NA 1.20, Nikon, USA), and the resulting fluorescence photons was collected by the same objective and passed through a dichroic mirror (540DRLP, Omega Optical, USA), a 50-µm pinhole, and a bandpass filter (645AF75, Omega Optical, USA). The fluorescence signals recorded by an avalanche photodiode (SPCM AQR15, EG&G, Canada) were transferred to a hardware digital correlator (Flex99R-480, Correlator.com, USA) to calculate autocorrelation functions. FCS curves were fitted by a home-made program written with Igor software (version 4.01, Wavemetrics, USA). 500 µl of solution, made by diluting samples into phosphate buffered saline (PBS, pH 7.4) to a final concentration of 1-10 nM, was used for each measurement.

Single Particle Imaging

Fluorescence images were acquired on an inverted microscope (TE2000U, Nikon, USA) with an oil immersion objective (100×, NA 1.4, Nikon, USA). The same laser for FCS measurements was used for the excitation. Fluorescence emission was filtered with a dichroic mirror (400-535-635 TBDR, Omega Optical, USA) and a bandpass filter (645AF75, Omega Optical, USA) before being detected by an intensified CCD (ICCD) camera (I-PentaMax, Roper Scientific, USA). Nanoparticle solutions were prepared by diluting into PBS to achieve a final concentration of 7-20 pM. Then, a KOH-cleaned coverslip was incubated with the solution for 5 min, and washed with PBS. 100 frames of images with an integration time of 300 ms were recorded by an ICCD at a gain set to 80.0.

FMNs for Synaptotagmin Labeling and Single Molecule Tracking

For this experiment, FMNs were conjugated with streptavidin through covalent linking of the surface thiol groups of FMNs with the amine groups of streptavidin using a crosslinker, sulfo-SMCC (Pierce Biotechnology). The FMN-streptavidin conjugates were purified with Microcon YM-100 filters and kept at 4° C. until the time of use. Rat hippocampal CA3-CA1 neurons were prepared in sparse culture, transfected with synaptophysin-EGFP on day 8th~10th and used on day 13. All experiments were performed at 25° C. For surface labeling of synaptotagmin in live neurons, biotinylated antibody against the lumenal domain of synaptotagmin I (105-311 BT, Synaptic System) were mixed with diluted Qdots®605-streptavidin (Invitrogen) or FMN-streptavidin (0.1-2 nM), and incubated with neurons for 2 min and then washed extensively for 20 min. The antibody was used after 1:800 dilution. Fluorescence detection of synapses and labeled synaptotagmin was performed using an inverted epi-fluorescence microscope (Nikon TE200, 1.3 NA objective) and an intensified charge-coupled device camera operating in gated acquisition mode (XR/Mega-10, Stanford Photonics). The light source is a Mercury Arc lamp. Brief pulses of illumination (470/40 nm) were gated by an optical switch. Fluorescence emission passed through a green (535/50 nm) or red (605/40 nm) band-pass filter and was acquired at 3 Hz with an exposure time of 100 ms. A 1.09 µm circle (eleven pixels), corresponding to 9 standard deviations of the point spread function of each sample was chosen as the standard ROI. The showed images are the averaged images of 200~500 sequential frames.

References, each of which is incorporated herein by reference for the corresponding discussion:

1. Lee, J.-H., Huh, Y.-M., Jun, Y.-w., Seo, J.-w, Jang, J.-t., Song, H.-T., Kim, S., Cho, E.-J., Yoon, H.-G, Suh, J.-S., Cheon, J. Artificially engineered magnetic nanoparticles for ultra-sensitive molecular imaging. *Nature Medicine* 13, 95-99 (2007).
2. Lewin, M., Carlesso, N., Tung, C., Tang, X., Cory, D., Scadden, D., Weissleder, R. Tat peptide derivaatized magnetic nanoparticles allow in vivo tracking and recovery of progenitor cells. *Nature Biotechnology* 18, 410-414 (2000).
3. Alivisatos, A. P. The use of nanocrystals in biological detection. *Nature Biotechnology* 22, 47-52 (2004).
4. Rhyner, M. N., Smith, A. M., Gao, X., Mao, H., Yang, L., Nie, S. Quantum dots and multifunctional nanoparticles: new contrast agents for tumor imaging. *Nanomedicine* 1, 1-9 (2006).
5. Seo, W. S., Lee, J. H., Sun, X., Suzuki, Y., Mann, D., Liu, Z., Terashima, M., Yang, P. C., Micconnell, M. V., Nishimura, D. G., Dai, H. FeCo/graphitic-shell nanocrystals as advanced magnetic-resonance-imaging and near-infrared agents. *Nature Materials* 5, 971-976 (2006).
6. Weissleder, R. Molecular Imaging in Cancer. *Science* 312, 1168-1171 (2006).
7. Massoud, T. F., Gambhir, S. S. Molecular imaging in living subjects: Seeing fundamental biological processes in a new light. *Genes & Development* 17, 545-580 (2003).
8. Moseley, M., Donnan, G. Multimodality Imaging. *Stroke* 35, 2632-2634 (2004).
9. Bakalova, R., Zhelev, Z., Aoki, I., Kanno, I. Designing quantum-dot probes. *Nature Photonics* 1, 487-489 (2007).
10. Kircher, M. F., Mahmood, U., King, R. S., Weissleder, R., Josephson, L. A Multimodal Nanoparticle for Preoperative Magnetic Resonance Imaging and Intraoperative Optical Brain Tumor Delineation. *Cancer Research* 63, 8122-8125 (2003).
11. Veiseh, O., Sun, C., Gunn, J., Kohler, N., Gabikian, P., Lee, D., Bhattarai, N., Ellenbogen, R., Sze, R., Hallahan, A., Olson, J., Zhang, M. Optical and MRI Multifunctional Nanoprobe for Targeting Gliomas. *Nano Letters* 5, 1003-1008 (2005).
12. Kelly, K. A., Allport, J. R., Tsourkas, A., Shinde-Patil, V. R., Josephson, L., Weissleder, R. Detection of Vascular Adhesion Molecule-1 Expression Using a Novel Multimodal Nanoparticle. *Circulation Research* 96, 327-336 (2005).
13. Tartaj, P., Morales, M. d. P., Verdaguer, S. V., Carreno, T. G., Serna, C. G. The preparation of magnetic nanoparticles for applications in biomedicine. *Journal of Physics D: Applied Physics* 36, 182-197 (2003).
14. Kostura, L., Kraitchman, D. L., Mackay, A. M., Pittenger, M. F., Bulte, J. W. M. Feridex Labeling of mesenchymal stem cells inhibits chondrogenesis but not adipogenesis or osteogenesis. *NMR IN Biomedicine* 17, 513-517 (2004).
15. Anzai, Y. Superparamagnetic Iron Oxide Nanoparticles Nodal Metastases and Beyond. *Topics in Magnetic Resonance Imaging* 15, 103-111 (2004).
16. Hyeon, T., Lee, S. S., Park, J., Chung, Y., Na, H. B. Synthesis of Highly Crystalline and Monodisperse Maghemite Nanocrystallites without a size-selection process. *Journal of the American Chemical Society* 123, 12798-12801 (2001).
17. Fu, A., Gu, W., Boussert, B., Koski, K., Gerion, D., Manna, L., Le Gros, M., Larabell, C. A., Alivisatos, A. P. Semiconductor Quantum Rods as Single Molecule Fluorescent Labels. *Nano Letters* 7, 179-182 (2007).
18. Fu, A. in *Chemistry* (University of California Berkeley, Berkeley, 2006).
19. Jun, Y.-w., Huh, Y.-m., Choi, J. S., Lee, J. H., Song, H. T., Kim, S. J., Yoon, S., Kim, K. S., Shin, J. S., Suh, J. S., Cheon, J. W. Nanoscale Size Effect of Magnetic Nanocrystals and Their Utilization for Cancer Diagnosis via Magnetic Resonance Imaging. *Journal of the American Chemical Society* 127, 5732-5733 (2005).
20. Karczmar, G. S., Fan, X., Hallaq, H. A., River, J. N., Tarlo, K., Kellar, K. E., Zamora, M., Schaeffer, C. R., Lipton, M. J. Functional and Anatomic Imaging of Tumor Vasculature: High-Resolution MR Spectroscopic Imaging Combined with a Superparamagnetic Contrast Agent. *Academic Radiology* 9, S115-S118 (2002).
21. Lakowicz, J. R. *Principles of Fluorescence Spectroscopy* (1983 Plenum Press, New York, 1986).
22. Burns, A., Ow, H., Wiesner, U. Fluorescent core-shell silica nanoparticles: towards "Lab on a Particle" architectures for nanobiotechnology. *Chemical Society Reviews* 35, 1028-1042 (2006).
23. Ow, H., Larson, D. R., Srivastava, M., Baird, B. A., Webb, W. W., Wiesner, U. Bright and Stable Core-Shell Fluorescent Silica Nanoparticles. *Nano Letters* 5, 113-117 (2005).
24. Haustein, E., Schwille, P. Ultrasensitive investigations of biological systems by fluorescence correlation spectroscopy. *Methods* 29, 153-166 (2003).
25. Magde, D., Elson, E., Webb, W. W. Thermodynamic Fluctuations in a Reacting System-Measurement by Fluorescence Correlation Spectroscopy. *Physical Review Letters* 29, 705-708 (1972).
26. Nirmal, M., Dabbousi B. O., Bawendi, M. G., Macklin, J. J., Trautman, J. K., Harris, T. D., Brus, L. E. Fluorescence Intermittency in single cadmium selenide nanocrystals. *Nature* 383, 802-804 (1996).
27. Bagshaw, C. R., Cherny, D. Blinking fluorophores: what do they tell us about protein dynamics. *Biochemical Society Transactions* 34, 979-982 (2006).
28. Rasnik, I., McKinney, S. A., Ha, T. Nonblinking and long-lasting single-molecule fluorescence imaging. *Nature Methods* 3, 891-893 (2006).
29. Min, W., English, B. P., Luo, G., Cherayil, B. J., Kou, S. C., Xie, x. S. Fluctuating Enzymes: Lessons from Single-Molecule Studies. *Acc. Chem. Res.* 38, 925-931 (2005).
30. Cui, B., Wu, C., Chen, L., Ramirez, A., Bearer, E. L., Li, W. P., Mobley, W. C., Chu, S. One at a time, live tracking of NGF axonal transport using quantum dots. *Proceedings of the National Academy of Sciences of the United States of America* 104, 13666-13671 (2007).
31. Chapman, E. R. How Does Synaptotagmin Trigger Neurotransmitter Release? *Annu. Rev. Biochem.* 77, 7.1-7.27 (2008).

Supplementary Information for Example 1

The surface silanization coating of the present disclosure is very versatile. SPIO nanoparticles made by many different methods can go through this surface modification and become water soluble and biocompatible. FIG. 1.6 is an example of SPIO nanoparticles that were made into the highly fluorescent magnetic nanoprobes through this surface silanization coating. These SPIOs were synthesized by oxidative decomposition of iron pentacarbonyl in the presence of trimethylamine N-oxide and oleic acid in hexadecane. The transmission electron micrograph of these SPIO is shown in FIG. 1.6*a*. Their size distribution is shown in FIG. 1.6*b*.

Fluorophores can be incorporated into silanized SPIO using many different approaches. In one of the approaches, nanoparticles were firstly covalently linked with biotin molecules, and then the fluorophores conjugated with streptavidin were bound to the nanoparticles through streptavidin-biotin association. In the gel-electrophoresis image of FIG. 1.7, mobilities of streptavidin-fluorophore incorporated SPIO nanoparticles were compared with that of un-incorporated streptavidin-fluorophores. Because of the bulky SPIO nanoparticles, the streptavidin-fluorophore-SPIO samples move slower than un-incorporated streptavidin-fluorophores. Such gel shift assay can prove the success of fluorophore incorporation. At the same time, the difference in fluorescent intensity of the streptavidin-fluorophore-SPIO samples and corresponding un-incorporated streptavidin fluorophores is illustrated, demonstrating the fluorescence protection/stabilization effect from silanized SPIO nanoparticles.

Fluorescent magnetic nanoprobes of the present disclosure have excellent fluorescence tunability. Any organic fluorophores with appropriate functional groups or molecular structures can be incorporated into the nanoprobes. FIG. 1.8 demonstrates an example of the tunability in both the excitation and emission spectra of these fluorescent magnetic nanoprobes with three representative emission colors of green, orange and near infrared. Such flexibility in terms of fluorophore incorporation can be useful in providing fluorescent magnetic nanoprobes that can be injected into living subjects and can be used in clinical applications. For example, the FDA approved fluorophore ICG (indocyanine green) can also be used to make these nanoparticles.

The high fluorescence of these fluorescent magnetic nanoprobes can be attributed mainly to two factors. One of the factors is the many available functional groups or active sites of the silanization coating that can be used to incorporate multiple fluorophores (up to hundreds) into the fluorescent magnetic nanoprobes. The other factor is the fluorescence protection or stabilization effect after fluorophores are incorporated into the silanization shell. FIG. 1.9 shows the fluorescence instability of various organic fluorophores, which is likely due to their chemical in-stability, including losing fluorescence after collision with active oxygen species in solution, and free rotation to certain molecular configurations with low fluorescence capability.

After being incorporated with silanized SPIO nanoparticles, the fluorescence of organic fluorophores is stabilized. One example of the fluorescence stabilization effect as a function of fluorophore concentration is shown in FIG. 1.10. Fluorophore-SPIO samples have higher fluorescence than the control un-incorporated fluorophores across a wide concentration range. The fluorescence intensity from fluorophore-SPIO samples is similar to that of a freshly prepared free fluorophore solution (in phosphate buffered saline at pH of 7.3). When the free fluorophores constantly lose their fluorescence signals with time, the fluorophore-SPIO solution retain their fluorescence signal.

The fluorescence of these fluorescent magnetic nanoparticles (FMN) is also characterized at single molecule level with fluorescence correlation spectroscopy (FCS). The sizes of FMN can also be derived from FCS. For samples characterized with FCS, the sizes range from about 15 nm to 37 nm. The sizes are similar to that of the commercial quantum dots. The fluorescence intensity of FMN in one sample was measured to be 1.6 times more than commercial quantum dots from the FCS experiment.

When directly imaging these FMN at single molecule level, they demonstrate desirable properties with bright, long lasting fluorescence signals with no blinking (fluorescence intermittency). FIG. 1.11 shows this property. When commercial quantum dots blink randomly, FMN constantly shows a high fluorescence signal. This property is necessary for single molecule long-term and continuous tracking of biological events. Fluorophores with this property are lacking. Semiconductor quantum dots blink, and organic fluorophores or engineered proteins photo-bleach in a much faster manner. Single nanoparticle fluorescence intensity was also obtained and compared for FMN and quantum dots from these single molecule fluorescence imaging experiments. As shown in FIG. 1.12, FMN shows average intensity of roughly 1.5 times of that of individual quantum dots, corresponding well with the intensity measurement using FCS.

Example 2

Fluorescent magnetic nanoparticles (FMNs) (also referred to as coated SPIO nanoparticles) described herein are very biocompatible. FMNs have an iron oxide core with the same basic composition as in FDA approved clinical MRI contrast agent Feridex™. The iron oxide core individually is coated with a silanization shell that is non-toxic and can be FDA approved. The fluorescence of FMNs is generated by incorporated organic fluorophores with very flexible fluorophore selection. The excellent biocompatibility and superior fluorescence and magnetic properties of FMNs make them very promising multifunctional nanoprobes for in vivo and even clinical molecular cancer targeting, imaging, and therapeutic applications. The following examples demonstrated their excellent capabilities towards such applications.

FMN with Both Surface Amino and Mercapto Functional Groups for Cancer Targeting, Imaging and Therapy A silanization process that renders nanoparticle surface with both mercapto and amino functional groups was developed to modify superparamagnetic iron oxide nanoparticles (SPIO). The surface amino groups are used to covalently incorporate NHS ether functionalized organic fluorophores to SPIO surface. The surface mercapto groups are used to conjugate cancer cell targeting molecules. These targeting molecules, either small peptide molecules or antibodies, are with amino functional groups, hence, they are able to conjugate to SPIO through common bioconjugation chemistry using a cross linker called sulfo-SMCC. By providing two functional groups on nanoparticle surface that bind separately to fluorophores and targeting molecules, the developed fluorescent magnetic nanoparticle (FMN) preparation process allows orthogonal control of nanoparticle fluorescence and cancer binding properties. FIG. 2.1 shows FMNs with surface RGD are specifically bound to cancer cells (U87MG, glioblastoma) that over-express $\alpha_v\beta_3$ integrin, a transmembrane receptor protein that is important for tumor growth and angiogenesis. In contrast, for SK-OV-3, the human ovarian cancer cell lines that have low number of surface $\alpha_v\beta_3$ integrins, there is no binding of FMNs to the cell surface under all 3 conditions.

These experiments confirm that FMNs can specifically label cancer cells for potential imaging and therapy applications.

FMN as Highly Sensitive In Vivo Fluorescent Imaging Agent

Incorporating of fluorophores with near Infrared (NIR) fluorophores such as Cy5.5 and Cy7 to silanized SPIO was also investigated. Fluorescence characterization in both PBS and Serum demonstrated that both FMN-Cy5.5 and FMN-Cy7 presented much stronger fluorescence than commercial Quantum Dot 705 nm (QD705) or Quantum Dot 800 nm (QD800) respectively. In general, around 20 fold signal increase from FMN-Cy5.5 and over 60 fold signal increase from FMN-Cy7 were observed. The strong fluorescence of FMN in the NIR region allows sensitive in vivo fluorescence imaging using FMNs. FIG. 2.2 shows the experimental results for preliminary characterization of in vivo fluorescence sensitivity of FMN-Cy5.5. 500 pM FMN can be easily detected. FMN-Cy7 presented similar detection sensitivity. The sensitivity is improved 20 times than the previously reported in vivo fluorescence imaging sensitivity of QD.

FMN as Highly Sensitive In Vivo MRI Contrast Agent

The capability of FMN for magnetic resonance imaging (MRI) was characterized using 7T MRI scanner. FMN shows high MR transverse relaxivity $r_2$ and MRI detection sensitivity. Small amount of samples, for example 2 pmol of nanoparticles, provide plenty of imaging contrast in vivo after intramuscular introduction of the sample. When a catheter is applied, contrast agent development can be imaged by MRI following multiple sample injections. (See FIG. 2.3) The high sensitivity of FMNs in providing MRI contrast will allow imaging using much less (up to a thousand times less) samples than some conventionally used dosage for MRI with SPIO contrast agents. In fact, the MRI sensitivity characterized down to 500 pM is similar to the sensitivity of FMNs for fluorescence imaging (500 pM). Hence, it is more practical and meaningful to pursue FMNs for correlated fluorescence and MRI cancer imaging.

FMN for Highly Sensitive and Correlated Fluorescence and MRI Imaging

FMNs with both high sensitivity for fluorescence and MRI imaging were investigated for correlated fluorescence and MRI imaging through in vivo experiments. Three samples with 1 nM, 500 pM and 0 sample concentration were implanted subcutaneously onto the back of a live mouse. Subsequently fluorescence optical imaging and MRI imaging were carried out. As shown in FIG. 2.4, the signal difference in the ROI (region of interest) outlined by dash circles for the 3 implanted samples were clearly observable. The detectable FMN concentration of 500 pM represents very high sensitivity for both fluorescence and MRI imaging, demonstrating significant improvements compared to previously documented fluorescent magnetic nanoparticles. Such high performance FMNs are desirable for clinical applications where MRI could be used for preoperative diagnostics and fluorescent imaging could be used to guide surgical intervention.

FMNs for Intravital Imaging

FMNs were also investigated for their in vivo molecular cancer targeting and imaging capabilities using an intravital microscope. Their high fluorescence allows such direct observation. For FMNs, the silanization shell thickness is tailorable, hence, the sizes of FMNs and individual particle fluorescence brightness are all controllable. Intravital microscopy allows direct observation of the interaction of FMNs with living subjects. Such direct observation will promote the understanding of FMNs in vivo behavior and is critical in design and optimization of FMNs for specific in vivo applications based on their size, surface molecules and pharmacokinetics. FIG. 2.5 shows individual FMNs with surface RGD specifically bound to $\alpha_v\beta_3$ integrin in the tumor (U87MG) neovasculature. Control samples of FMNs with surface RAD had minimal bounding when observed under the same experimental condition.

FMNs for Magnetically Enhanced Cancer Targeting, Imaging and Therapy

FMNs can respond to external magnetic field gradient, hence their cancer targeting capability can be further enhanced with magnetic forces for improved imaging and therapeutic applications (See FIG. 2.6). In one experiment, magnetic microstructures were utilized to provide the external magnetic control. These magnetic microstructures could be pre-treated with biocompatible coating, hence cell culture on top of the microstructure was possible. Individual FMN was observed responding to the magnetic field gradient of the magnetic microstructure. Very strong forces were generated that attracted significant amounts of FMNs to the edge of the magnetic microstructure. The magnitude of the force can be precisely controlled by altering the size and shape of the features on the magnetic microstructure and by adjusting the spacing between FMNs and the magnetic microstructure. The magnetic microstructure can also be designed compatible with in vivo molecular cancer imaging applications, for example, on a highly transparent or flexible film. In fact, a magnetic stand based on such magnetic microstructures can be clinically useful to enhance cancer targeting, imaging and therapeutic effects of magnetic nanoparticles. The superior magnetic properties achievable by FMNs make them ideal candidates to be combined in potential clinical applications with such magnetic control.

FMNs for Magnetically Enhanced T-Cell Trafficking, Cancer Imaging and Therapy.

Because of the versatility and flexibility in the preparation method, FMNs with different sizes and surface properties can be synthesized (See FIG. 2.7). This allows specifically tune FMN property for cellular uptake. In this experiment, FMNs with hydrodynamic sizes of 45 nm, and surface mercapto groups were able to be loaded inside T-cells with multiple methods, including transfection with chemical agents and electroporation. For large particles with sizes in 400 to 600 nm range, and for FMNs containing surface amino groups, T-cell uptake was found to be difficult. FMNs loaded T-cells could respond to a simple permanent magnet. Hence, T-cell trafficking, and its function for cancer imaging and therapy can be magnetically enhanced through the use of FMNs.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim the following:

1. A nanoprobe, comprising:
a superparamagnetic iron oxide (SPIO) nanoparticle, wherein the SPIO nanoparticle has a silanization coating on the surface of the SPIO nanoparticle, wherein the silanization coating is about 5 to about 1000 nm thick, or more, does not include silicates or silica, and is made of cross-linked trimethoxyl silanes that are cross-linked with two or more different types of functional groups, wherein the functional groups are selected from the group consisting of: an amino group, a mercapto group, a carboxyl group, a phosphonate group, a polyethylene oxide group (PEG), a hydroxyl group, an alkyl group and a combination thereof.

2. The nanoprobe of claim 1, further comprising at least ten fluorescent compounds attached to the silanization coating.

3. The nanoprobe of claim 1, wherein the SPIO nanoparticle has a diameter of about 3 nm to 40 nm.

4. The nanoprobe of claim 1, wherein silanization coating is amorphous and controllable to about 5 nm to 500 nm thick.

5. The nanoprobe of claim 1, wherein the SPIO nanoparticle is a product of an oxidative decomposition of iron pentacarbonyl with a compound selected from the group consisting of: trimethylamine oxide, oleic acid, hexadecane, and a combination thereof.

6. The nanoprobe of claim 2, wherein the fluorescent compounds are attached to the silanization coating through an interaction selected from the group consisting of: covalent bond, a non-covalent bond, an ionic bond, a chelation interaction, a hydrophobic interaction, a hydrophilic interaction, a charge-charge interaction, and a π-stacking interaction.

7. The nanoprobe of claim 1, wherein the SPIO nanoparticles are precipitated with isopropanol prior to silanization.

8. The nanoprobe of claim 2, wherein the fluorescent compounds are attached to the silanization coating via at least one of the types of functional group.

9. The nanoprobe of claim 1, wherein the silanization coating includes biotin.

10. The nanoprobe of claim 9, wherein a streptavidin-fluorescent compound is attached to the silanization coating via biotin.

11. The nanoprobe of claim 1, wherein a targeting moiety is attached to the silanization coating, wherein the targeting moiety has an affinity for a target.

12. The nanoprobe of claim 2, wherein the fluorescent compound is a fluorophore.

13. The nanoprobe of claim 1, wherein the iron oxide nanoparticle comprises one or more particles composed of a phase selected from the group consisting of: a maghemite (($\gamma$-$Fe_2O_3$) phase, a magnetite ($Fe_3O_4$) phase, and a combination of both phases.

14. The nanoprobe of claim 1, wherein at least one type of fluorescent compound is attached to one type of functional group; and at least one second type of compound is attached to the other type of functional group, wherein the second type of compound is selected from: a second type of fluorescent compound, a targeting moiety, a drug, a therapeutic agent, a radiological agent, a chemological agent, a small molecule drug, and a biological agent.

15. The nanoprobe of claim 1, wherein the silanization coating does not change the magnetic properties of the original SPIO nanoparticle.

16. The nanoprobe of claim 1, wherein the silanization coating includes amino functional groups and mercapto functional groups.

17. The nanoprobe of claim 16, wherein a portion of the amino functional groups are attached to fluorescent compounds, where each amino functional group of the portion is attached to a fluorescent compound; and a portion of the mercapto functional groups are attached to targeting moieties, wherein each mercapto functional group of the portion is attached to a targeting moiety.

18. A nanoprobe, comprising:
a superparamagnetic iron oxide (SPIO) nanoparticle, wherein the SPIO nanoparticle has a silanization coating on the surface of the SPIO nanoparticle, wherein the silanization coating is about 5 nm to 1000 nm thick, does not include silicates or silica, and includes two or more different functional groups, wherein the functional groups are selected from the group consisting of: an amino group, a mercapto group, a carboxyl group, a phosphonate group, a polyethylene oxide group (PEG), a hydroxyl group, an alkyl group and a combination thereof, and
at least ten fluorescent compounds attached to the functional groups of the silanization coating, wherein each fluorescent compound is attached to the silanization coating via a functional group, and wherein the silanization coating provides a protective effect for the fluorescent compound.

* * * * *